US006022745A

United States Patent [19]
Aldovini et al.

[11] Patent Number: 6,022,745
[45] Date of Patent: *Feb. 8, 2000

[54] HOMOLOGOUSLY RECOMBINANT SLOW GROWING MYCOBACTERIA AND USES THEREFOR

[75] Inventors: Anna Aldovini; Richard A. Young, both of Weston, Mass.

[73] Assignee: Whitehead Institute for Biomedical Research, Cambridge, Mass.

[*] Notice: This patent is subject to a terminal disclaimer.

[21] Appl. No.: 08/471,869

[22] Filed: Jun. 7, 1995

Related U.S. Application Data

[63] Continuation of application No. 08/095,734, Jul. 22, 1993, Pat. No. 5,807,723, which is a continuation-in-part of application No. 07/711,334, Jun. 6, 1991, abandoned, which is a continuation-in-part of application No. 07/367,894, Jun. 19, 1989, abandoned, which is a continuation-in-part of application No. 07/361,944, Jun. 5, 1989, Pat. No. 5,504,005, which is a continuation-in-part of application No. 07/223,089, Jul. 22, 1988, abandoned, and application No. 07/216,390, Jul. 7, 1988, abandoned.

[51] Int. Cl.$^7$ ............................ C12N 15/64; C12N 13/00; C12N 1/21; C12N 15/31

[52] U.S. Cl. .................. 435/440; 435/173.6; 435/252.3; 435/253.1; 536/23.5; 536/23.7

[58] Field of Search ............................... 435/69.1, 320.1, 435/253.1, 172.3, 440, 252.3, 173.6; 536/23.5, 23.7

[56] References Cited

U.S. PATENT DOCUMENTS

| | | | |
|---|---|---|---|
| 4,906,742 | 3/1990 | Young et al. | 536/23.7 |
| 4,910,140 | 3/1990 | Dower | 435/488 |
| 4,952,500 | 8/1990 | Finnerty et al. | 435/69.1 |

FOREIGN PATENT DOCUMENTS

| | | |
|---|---|---|
| 0127153 | 12/1984 | European Pat. Off. |
| WO 88/06626 | 9/1988 | WIPO |
| WO 90/00594 | 1/1990 | WIPO |
| WO 90/15873 | 12/1990 | WIPO |

OTHER PUBLICATIONS

Jacobs et al. Introduction of foreign DNa into mycobacteria using a shuttle phasmid. Nature vol. 327 pp. 532–535, 1987.
Weisberg et al. Lambda II Hendrix et al. Eds., Cold Spring Harbor Lab. (1983) 211–250 "Site specific Recomb. in Phge Labda."
Udou et al J. Bact. 151:1035–1039 (1982).
Lugosi, L., "Analysis of Variables of Plasmid Transformation of a Bacterial Vaccine: Studies on Recombinant BCG", *Vaccine*, 8:145–149 (1990).
Lugosi, L., et al., "Genetic Transformation of BCG", *Tubercle*, 70:159–170 (1989).
Lugosi, L., et al., "Transformation of BCG with Plasmid DNA", *Acta Leprologica*, 7(Suppl.1):256–267 (1989).
Jacobs, W.R., et al., "Development of Genetic Systems for the Mycobacteria", *Acta Leprologica*, 7(Suppl.1):203–207 (1989).

Mizuguchi, Y., et al., "Establishment of a Host–Vector System in *Mycobacterium Bovis* BCG", *Kekkaku*, 66(9):607–613 (1991).
Goto, Y., et al., "Development of a New Host Vector System in Mycobacteria", *FEMS Microbiology Letters* 83:277–282(1991).
Houssaini–Iraqui, M., et al., "Cloning and Expression of *Mycobacterium aurum* Carotenogenesis Genes in *Mycobacterium smegmatis*", *FEMS Microbiolgy Letters*, 90:239–244 (1992).
"ElectroCell Manipulator 600 Electroporation System", Operating Manual (Biotechnologies & Experimental Research Inc., San Diego, CA), pp. 27–32 (1991).
Hinshelwood, S. and Stoker, N.G., "An *Escherichia coli– Mycobacterium* Shuttle Cosmid Vector, pMSC1", *Gene*, 110:115–118 (1992).
Trevors, J.T., et al., "Electrotransformation of Bacteria". In *Guide to Electroporation and Electrofusion*, D.C. Chang et al., eds. (CA: Academic Press, Inc.), pp. 274–276 (1992).
Dower, W.J., et al., "Protocols for the Transformation of Bacteria by Electroporation". In *Guide to Electroporation and Electrofusion*, D.C. Chang et al., eds. (CA: Academic Press, Inc.), pp. 485–499 (1992).
Jacobs, W.R. et al., "Expression of *Mycobacterium leprae* Genes From a *Streptococcus mutans* Promoter in *Escherichia coli* K–12", *Proc. Natl. Acad. Sci. USA*, 83:1926–1930 (1986).
Husson, R.N. et al., "Genes for the Major Protein Antigens of *Mycobacterium tuberculosis*: The Etiologic Agents of Tuberculosis and Leprosy Share An Immunodominant Antigen", *Proc. Natl. Acad. Sci. USA*, 84:1679–1683 (1987).
Shinnick, T.M. et al., "The Etiologic Agents of Leprosy and Tuberculosis Share an Immunoreactive Antigen with the Vaccine Strain *Mycobacterium bovis* BCG", *Infection & Immunity*, 55(8):1932–1935 (1987).
Lu, M.C. et al., "Genes for Immunodominant Protein Antigens Are Highly Homologous in *Mycobacterium tuberculosis, Mycobacterium africanum*, and the vaccine strain *Mycobacterium bovis* BCG", *Infection & Immunity*, 55:2378–2382 (1987).

(List continued on next page.)

*Primary Examiner*—John S. Brusca
*Attorney, Agent, or Firm*—Hamilton, Brook, Smith & Reynolds, P.C.

[57] ABSTRACT

A method of transforming slow-growing mycobacteria, such as *M. bovis* BCG, *M. leprae, M. tuberculosis M. avium, M. intracellulare* and *M. africanum*; a method of manipulating genomic DNA of slow-growing mycobacteria through homologous recombination; a method of producing homologously recombinant (HR) slow-growing mycobacteria in which heterologous DNA is integrated into the genomic DNA at a homologous locus; homologously recombinant (HR) slow-growing mycobacteria having heterologous DNA integrated into their genomic DNA at a homologous locus; and mycobacterial DNA useful as a genetic marker.

29 Claims, 7 Drawing Sheets

OTHER PUBLICATIONS

Lamb, F.I. et al., "Heterologous Expression of the 65–Kilodalton Antigen of *Mycobacterium leprae* and Murine T–Cell Responses to the Gene Product", *Infection & Immunity*, 56:1237–1241 (1988).

Sirakova, T.D. et al., "Molecular Cloning of Mycobacterial Promoters in *Escherichia coli*", *FEMS Micro. Lett.*, 59:153–156 (1989).

Stoker, N.G. et al., "High Level Expression of Genes Cloned in Phage λgt11", *Gene*, 78:93–99.

Borremans, M. et al., "Cloning, Sequence Determination, and Expression of a 32–Kilodalton–Protein Gene of *Mycobacterium tuberculosis*", *Infection & Immunity*, 57:3123–3130 (1989).

Husson, R.N. et al., "Gene Replacement and Expression of Foreign DNA in Mycobacteria", *J. Bacteriol.*, 172:519–524 (1990).

Snapper, S.B. et al., "Lysogeny and Transformation in Mycobacteria: Stable Expression of Foreign Genes", *Proc. Natl. Acad. Sci. USA*, 85:6987–6991 (1988).

Vodkin, M.H. et al., "A Heat Shock Operon in *Coxiella burnetii* Produces a Major Antigen Homologous to a Protein in Both Mycobacteria and *Escherichia coli*", *J. Bacteriol.* 170:1227–1234 (1988).

Baird, P.N. et al., "Cloning and sequence Analysis of the 10 kDa Antigen Gene of *Mycobacterium tuberculosis*", *J. Gen. Microbiol.*, 135:931–939 (1989).

Hone, D. et a., "A Chromosomal Integration System for Stabilization of Heterologous Genes in *Salmonella* Based Vaccine Strains", *Microbial Pathogenesis*, 5:407–418 (1988).

Mackett, M. et al., "General Method for Production and Selection of Infectious Vaccinia Virus Recombinants Expressing Foreign Genes", *J. Virol.*, 49:857–864 (1984).

Clements, J.D. et al., "Construction of a Potential Live Oral Bivalent Vaccine for Typhoid Fever and Cholera–*Escherichia coli*–Related Diarrheas", *Infection & Immunity*, 46:564–569 (1984).

Young, R.A. et al., "Dissection of *Mycobacterium tuberculosis* Antigens Using Recombinant DNA", *Proc. Natl. Acad. Sci. USA*, 82:2583–2587 (1985).

Lindquist, S. et al., "The Heat–Shock Proteins", *Ann. Rev. Genet.*, 22:631–677 (1988).

Lathigra, R.B. et al., "A Gene From *Mycobacterium tuberculosis* Which Is Homologous to the DnaJ Heat Shock Protein of *E. coli*", *Nucleic Acids Res.*, 16:1636 (1988).

Burke, J.F., "An Assay for Transient Gene Expression in Transfected *Drosophila* Cells, Using [$^3$H] Guanine Incorporation", *The EMBO J.*, 3:2549–2554 (1984).

Suarez, J.E. et al., "DNA Cloning in Streptomyces: A Bifunctional Replicon Comprising pBR322 Inserted Into A Streptomyces: A Bifunctional Replicon Comprising pBR322 Inserted Into A Streptomyces Phage", *Nature*, 286:527–529 (1980).

Post, L.E. et al., "A Generalized Technique for Delection of Specific Genes in Large Genomes: α Gene 22 of Herpes simplex Virus 1 Is Not Essential for Growth", *Cell*, 25:227–232 (1981).

Crawford, J.T. et al., "Characterization of Plasmids from Strains of *Mycobacterium avium–intracellulare*", *Rev. Infec. Diseases*, 3(5):949–952 (1981).

Lotte, A. et al., "BCG Complications; Estimates of the Risks among Vaccinated Subjects and Statistical Analysis of Their Main Characteristics", *Adv. in Tuberculosis Res.*, 21:107–193 (1984).

Labidi, A. et al., "Plasmid Profiles of *Mycobacterium fortuitum* Complex Isolates", *Current Microbiol.*, 11:235–240 (1984).

Crawford, J.T. et al., "Restriction Endonuclease Mapping and Cloning of *Mycobacterium intracellulare* plasmid pLR7", *Gene*, 27:331–332 (1984).

Labidi, A. et al., "Cloning and Expression of Mycobacterial Plasmid DNA in *Escherichia coli*", *FEMS Microbiol. Lett.*, 30:221–225 (1985).

Labidi, A. et al., "Restriction Endonuclease Mapping and Cloning of *Mycobacterium Fortuitum* var. *Fortuitum* Plasmid pAL5000", *Ann. Inst. Pasteur/Microbiol.*, 136B:209–215 (1985).

Crawford, J.T. et al., "Analysis of Plasmids in *Mycobacterium avium–intracellulare* Isolates from Persons With Acquired Immunodeficiency Syndrome", *Am. Rev. Respir. Dis.*, 134:659–661 (1986).

Jacobs, W.R. et al., "In Vivo Repackaging of Recombinant Cosmid Molecules for Analyses of *Salmonella typhimurium*, *Streptococcus mutans*, and Mycobacterial Genomic Libraries", *Infection & Immunity*, 52:101–109 (1986).

Timme, T.L. et al., "Induction of Bacteriophage from Members of the *Mycobacterium avium, Mycobacterium intracellulare, Mycobacterium scrofulaceum* Serocomplex", *J. Gen. Microbiol.*, 130:2059–2066 (1984).

Husson, R.N. et al., "Gene Replacement and Expression of Foreign DNA in Mycobacteria", *J. Bacteriol.*, 172:519–524 (1990).

Young, D.B. et al., "Leprosy, Tuberculosis and the New Genetics", *J. Bacteriol.*, 175:1–6 (1993).

Kalpana, G.V. et al., "Insertional Mutagenesis and Illegitimate Recombination in Mycobacteria", *Proc. Natl. Acad. Sci. USA*, 88:5433–5437 (1991).

Hermans, J. et al., "Transformation of *Mycobacterium aurum* by electroporation: the use of glycine, lysozyme and isonicotinic acid hydrazide in enhancing transformation efficiency," *FEMS Microbiology Letters* 72:221–224 (1990).

Jacobs, William R., Jr., et al., "Genetic Systems for Mycobacteria," *Methods in Enzymology* 204:537–555 (1991).

Aldovini, Anna et al., "The *uraA* Locus and Homologous Recombination in *Mycobacterium bovis* BCG," *Journal of Bacteriology* 175(22):7282–7289 (1993).

Lee, M.H., et al., "Site–specific integration of mycobacteriophage L5: Integration–proficient vectors for *Mycobacterium smegmatis, Mycobacterium tuberculosis*, and bacille Calmette–Guérin," *Proc. Natl. Acad. Sci. USA* 88:3111–3115 (1991).

Ramakrishnan, T. and Shaila, M.S., "Interfamilial Transfer of Amber Suppressor Gene for the Isolation of Amber Mutants of Mycobacteriophage I3", *Arch. Microbiol.*, 120:301–302 (1979).

Chassy, B.M. and Flickinger, J.L., "Transformation of *Lactobacillus casei* by electroporation", *FEMS Microbiology Letters* 44:173–177 (1987).

Hopwood, D.A. et al., "Cloning of DNA: Choice of Vectors and Strategies", In *Genetic Manipulation of Streptomyces: A Laboratory Manual*, The John Innes Foundation, Norwich, pp.162–179 (1985).

West, Robert W., Jr., "Molecular Cloning Vectors of Saccharomyces: Generalized Cloning Vectors". In *Vectors: A Survey of Molecular Cloning Vectors and Their Uses*, R.L. Rodriguez and D.T. Denhardt, Editors (Butterworth Publishers, Boston, MA) pp. 387–404 (1987).

```
GAGCTCGACCCCGCCGCCGAAACAGAGGTGGCCCCGCAGACCGAAAGGCCCAAGGTGCTG      60
 E   L   D   P   A   A   E   T   E   V   A   P   Q   T   E   R   P   K   V   L

ATCCTCGGTTCGGGGCCCAATCGGATCGGCCAGGGTATCGAGTTCGACTACAGCTGCGTA    120
 I   L   G   S   G   P   N   R   I   G   Q   G   I   E   F   D   Y   S   C   V

CACGCGGCAACCACGTTGAGCCAGGCTGGCTTTGAGACCGTGATGGTCAACTGCAACCCG    180
 H   A   A   T   T   L   S   Q   A   G   F   E   T   V   M   V   N   C   N   P

GAGACCATGGTGTCCACCGACTTCGACACCGCGGACAGGTTGTACTTCGAGCCGTTGACG    240
 E   T   M   V   S   T   D   F   D   T   A   D   R   L   Y   F   E   P   L   T

TTCGAGGACGTCTTGGAGGTCTACCACGCCGAAATGGAATCCGGTAGCGGTGGCCCGGGA    300
 F   E   D   V   L   E   V   Y   H   A   E   M   E   S   G   S   G   G   P   G

GTGGCCGGCGTCATCGTGCAGCTCGGCGGCCAGACCCCGCTCGGCTGGCGCACCGGCTCG    360
 V   A   G   V   I   V   Q   L   G   G   Q   T   P   L   G   W   R   T   G   S

CCGACGCCGGGTCCCGCTCGTGGGCACCCACCGGAGGCCATCGACCTGGCCGAGGATGCG    420
 P   T   P   G   P   A   R   G   H   P   P   E   A   I   D   L   A   E   D   A

GCCGTTCGGCGACCTGCTGAGCGAGGACTGCCGGCGCCAAAGTACGGCACCGCAACCACT    480
 A   V   R   R   P   A   E   R   G   L   P   A   P   K   Y   G   T   A   T   T

TTCGCCCAGGCCCGCCGGATCGCCGAGGAGATCGGCTATCCGGTGCTGGTGCGGCCGTCG    540
 F   A   Q   A   R   R   I   A   E   E   I   G   Y   P   V   L   V   R   P   S

TATGTGCTCGGTGGTCGCGGCATGGAGATCGTGTATGACGAAGAAACGTTGCAGGGCTAC    600
 Y   V   L   G   G   R   G   M   E   I   V   Y   D   E   E   T   L   Q   G   Y

ATCACCCGCGCCACTCAGCTATCCCCCGAACACCCGGTGCTCGTGCACCGCTTCCTCGAG    660
 I   T   R   A   T   Q   L   S   P   E   H   P   V   L   V   H   R   F   L   E

GACGCGGTCGAGATCGACGTCGACGCTCTGTGTGATGGCGCCGAGGTCTATATCGGCGGA    720
 D   A   V   E   I   D   V   D   A   L   C   D   G   A   E   V   Y   I   G   G

ATCATGGAGCACATCGAGGAGGCCGGCATCCACTCCGGTGACTCGGCCTGTGCGCTGCCA    780
 I   M   E   H   I   E   E   A   G   I   H   S   G   D   S   A   C   A   L   P

CCGGTCACGTTGGGCCGCAGCGACATCGAGAAGGTGCGTAAGGCCACTGAAGCCATTGCG    840
 P   V   T   L   G   R   S   D   I   E   K   V   R   K   A   T   E   A   I   A

CATGGCATCGGCGTGGTGGGCTGCTCAACGTGCAGTCCGCGCTCAAGGATGACGTGCTC    900
 H   G   I   G   V   V   G   L   L   N   V   Q   S   A   L   K   D   D   V   L

TACGTCCTGGAAGCCAACCCGAGAGCGAGCCGTACCGTTCCGTTTGTATCCAAGGCCACA    960
 Y   V   L   E   A   N   P   R   A   S   R   T   V   P   F   V   S   K   A   T

GCGGTGCCACTCGCCAAGGCATGCGCCCGGATCATGTTGGGCGCCACCATTGCCCAGCTG   1020
 A   V   P   L   A   K   A   C   A   R   I   M   L   G   A   T   I   A   Q   L

CGCGCCGAAGGCTTGCTGGCGGTCACCGGGGATGGCGCCCACGCGGCGCGAAACGCCCCC   1080
 R   A   E   G   L   L   A   V   T   G   D   G   A   H   A   A   R   N   A   P

ATCGCGGTCAACCAGGCCGTGTTGCCGTTTCACCGGTTCCGGCGCGCCGACGGGGCCGCC   1140
 I   A   V   N   Q   A   V   L   P   F   H   R   F   R   R   A   D   G   A   A

ATCGACTCGCTACTCGGCCCGGAGATGAAATCGACCGGCGAGGTGATGGGCATCGACCGC   1200
 I   D   S   L   L   G   P   E   M   K   S   T   G   E   V   M   G   I   D   R

GACTTCGGCAGCCGGTTCGCCAAGAGCCAGACCGCCGCCTACGGGTCGCTGCCGGCCCAG   1260
 D   F   G   S   R   F   A   K   S   Q   T   A   A   Y   G   S   L   P   A   Q
```

FIG. 2A

```
GGCACAGTGTTCGTGTCGGTGGCCAACCGGGACAAGCGGTCGCTGGTGTTTCCGGTCAAA    1320
 G  T  V  F  V  S  V  A  N  R  D  K  R  S  L  V  F  P  V  K

CGATTGGCCCACCTGGGTTTTCGCGTCCTTGCCACCGAAGCACCGCAGAGATCTTGCGCC    1380
 R  L  A  H  L  G  F  R  V  L  A  T  E  A  P  Q  R  S  C  A

GCAACGGTATTCCCTGCGACGACGTCCGCAAACATTTCGAGCCGGCGCAGCCCGGCCGCC    1440
 A  T  V  F  P  A  T  T  S  A  N  I  S  S  R  R  S  P  A  A

CCACAATGTCGGCGGTGGACGCGATCCGAGCCGGCGAGGTCAACATGGTGATCAACACTC    1500
 P  Q  C  R  R  W  T  R  S  E  P  A  R  S  T  W

CCTATGGCAACTCCGGTCCGCGCATCGACGGCTATGAGATCCGTTCGGCGGCGGTGGCCG    1560

GCAACATCCCGTGCATCACCACGGTGCAGGGCGCATCCGCCGCCGTGCAGGGGATAGAGG    1620

CCGGGATCCGCGGCGACATCGGGGTGCGCTCCCTGCAGGAGCTGCACCGGGTGATCGGGG    1680

GCGTCGAGCGGTGACCGGGTTCGGTCTCCGGTTGGCCGAGGCAAAGGCACGCCGCGGCCC    1740
             M  T  G  F  G  L  R  L  A  E  A  K  A  R  R  G  P

GTTGTGTCTGGGCATCGATCCGCATCCCGAGCTGCTGCGGGGCTGGGATCTGGCGACCAC    1800
 L  C  L  G  I  D  P  H  P  E  L  L  R  G  W  D  L  A  T  T

GGCCGACGGGCTGGCCGCGTTCTGCGACATCTGCGTACGGGCCTTCGCTGATTTCGCGGT    1860
 A  D  G  L  A  A  F  C  D  I  C  V  R  A  F  A  D  F  A  V

GGTCAAACCGCAGGTGGCGTTTTTTGAGTCATACGGGGCTGCCGGATTCGCGGTGCTGGA    1920
 V  K  P  Q  V  A  F  F  E  S  Y  G  A  A  G  F  A  V  L  E

GCGCACCATCGCGGAACTGCGGGCCGCAGACGTGCTGGTGTTGGCCGACGCCAAGCGCGG    1980
 R  T  I  A  E  L  R  A  A  D  V  L  V  L  A  D  A  K  R  G

CGACATTGGGGCGACCATGTCGGCGTATGCGACGGCCTGGGTGGGCGACTCGCCGCTGGC    2040
 D  I  G  A  T  M  S  A  Y  A  T  A  W  V  G  D  S  P  L  A

CGCCGACGCCGTGACGGCCTCGCCCTATTTGGGCTTCGGTTCGCTGCGGCCGCTGCTAGA    2100
 A  D  A  V  T  A  S  P  Y  L  G  F  G  S  L  R  P  L  L  E

GGTCGCGGCCGCCCACGGCCGAGGGGTGTTCGTGCTGGCGGCCACCTCCAATCCCGAGGG    2160
 V  A  A  A  H  G  R  G  V  F  V  L  A  A  T  S  N  P  E  G

TGCGGCGGTGCAGAATGCCGCCGCCGACGGCCGCAGCGTGGCCCAGTTGGTCGTGGACCA    2220
 A  A  V  Q  N  A  A  A  D  G  R  S  V  A  Q  L  V  V  D  Q

GGTGGGGGCGGCCAACGAGGCGGCAGGACCCGGGCCCGGATCCATCGGCGTGGTCGTCGG    2280
 V  G  A  A  N  E  A  A  G  P  G  P  G  S  I  G  V  V  V  G

CGCAACGGCGCCACAGGCCCCCGATCTCAGCGCCTTCACCGGGCCGGTGCTGGTGCCCGG    2340
 A  T  A  P  Q  A  P  D  L  S  A  F  T  G  P  V  L  V  P  G

CGTGGGGGTGCAGGGCGGGCGCCCGGAGGCGCTGGGCGGTCTGGGCGGGGCCGCATCGAG    2400
 V  G  V  Q  G  G  R  P  E  A  L  G  G  L  G  G  A  A  S  S

CCAGCTGTTGCCCGCGGTGGCGCGCGAGGTCTTGCGGGCCGGCCCCGGCGTGCCCGAATT    2460
 Q  L  L  P  A  V  A  R  E  V  L  R  A  G  P  G  V  P  E  L

GCGCGCCGCGGGCGAACGGATGCGCGATGCCGTCGCCTATCTCGCTGCCGTGTAGCGGGT    2520
 R  A  A  G  E  R  M  R  D  A  V  A  Y  L  A  A  V
```

FIG. 2B

```
GCCCTGCCACCGCGCCGCTAAATCCCACCAGCATGGGGTGGTGAGCCCAGCGCTCGTGTG    2580

ACCAAACTCACCGCCCTGGGCCGTCGTCACGCTGTGTTAACCTCTCGTTCAAATGATATT    2640

CATATTCAATAGTGGCGCTAAGTGTCCGGTTGAATCCCCGTTGAACCCCCAACAGATGGA    2700

GTCTGTGTCGTGACGTTGCGAGTCGTTCCCGAAAGCCTGGCAGGCGCCAGCGCTGCCATC    2760

GAAGCAGTGACCGCTCGCCTGGCCGCCGCGCACGCCGCGGCGGCCCCGTTTATCGCGGCG    2820

GTCATCCCGCCTGGGTCCGACTCGGTTTCGGTGTGCAACGCCGTTGAGTTCAGCGTTCAC    2880

GGTAGTCAGCATGTGGCAATGGCCGCTCAGGGGGTTGAGGAGCTCGGCCGCTCGGGGGTC    2940
         M  W  Q  W  P  L  R  G  L  R  S  S  A  A  R  G  S

GGGGTGGCCGAATCGGGTGCCAGTTATGCCGCTAGGATGCGCTGGCGGCGGCGTCGTATC    3000
 G  W  P  N  R  V  P  V  M  P  L  G  C  A  G  G  G  V  V  S

TCAGCGGTGGGCTATGACCGAGCCGTGGATAGCCTTCCCTCCCGAGGTGCACTCGGCGAT    3060
 Q  R  W  A  M  T  E  P  W  I  A  F  P  P  E  V  H  S  A  M

GCTGAACTACGGTGCGGGCGTTGGGCCGATGTTGATCTCCGCCACGCAGAATGGGGAGCT    3120
 L  N  Y  G  A  G  V  G  P  M  L  I  S  A  T  Q  N  G  E  L

CAGCGCCCAATACGCAGAAGCGGCATCCGAGGTCGAGGAATTGTTGGGGGTGGTGGCCTC    3180
 S  A  Q  Y  A  E  A  A  S  E  V  E  E  L  L  G  V  V  A  S

CGAGGGATGGCAGGGGCAAGCCGCCGAGGCGTTAGTCGCCGCGTACATGCCGTTTCTGGC    3240
 E  G  W  Q  G  Q  A  A  E  A  L  V  A  A  Y  M  P  F  L  A

GTGGCTGATCCAAGCCAGCGCCGACTGCGTGGAAATGGCCGCCCAGCAACACGCCGTCAT    3300
 W  L  I  Q  A  S  A  D  C  V  E  M  A  A  Q  Q  H  A  V  I

CGAGGCCTACACTGCCGCGGTAGAGCTGATGCCTACTCAGGTCGAACTGGCCGCCAACCA    3360
 E  A  Y  T  A  A  V  E  L  M  P  T  Q  V  E  L  A  A  N  Q

AATCAAGCTCGCGGTGTTGGTAGCGACCAATTTCTTTGGCATCAACACCATTCCCATTGC    3420
 I  K  L  A  V  L  V  A  T  N  F  F  G  I  N  T  I  P  I  A

GATCAATGAGGCCGAGTACGTGGAGATGTGGGTTCGGGCCGCCACCACGATGGCGACCTA    3480
 I  N  E  A  E  Y  V  E  M  W  V  R  A  A  T  T  M  A  T  Y

TTCAACAGTCTCCAGATCGGCGCTCTCCGCGATGCCGCACACCAGCCCCCCGCCGCTGAT    3540
 S  T  V  S  R  S  A  L  S  A  M  P  H  T  S  P  P  P  L  I

CCTGAAATCCGATGAACTGCTCCCCGACACCGGGGAGGACTCCGATGAAGACGGCCACAA    3600
 L  K  S  D  E  L  L  P  D  T  G  E  D  S  D  E  D  G  H  N

CCATGGCGGTCACAGTCATGGCGGTCACGCCAGGATGATCGATAACTTCTTTGCCGAAAT    3660
 H  G  G  H  S  H  G  G  H  A  R  M  I  D  N  F  F  A  E  I

CCTGCGTGGCGTCAGCGCGGGCCGCATTGTTTGGGACCCCGTCAACGGCACCCTCAACGG    3720
 L  R  G  V  S  A  G  R  I  V  W  D  P  V  N  G  T  L  N  G

ACTCGACTACGACGATTACGTCTACCCCGGTCACGCGATCTGGTGGCTGGCTCGAGGCCT    3780
 L  D  Y  D  D  Y  V  Y  P  G  H  A  I  W  W  L  A  R  G  L
```

FIG. 2C

```
CGAGTTTTTTTCAGGATGGTGAACAATTTGGCGAACTGTTGTTCACCAATCCGACTGGGGC   3840
E  F  F  Q  D  G  E  Q  F  G  E  L  L  F  T  N  P  T  G  A

TTTTCAGTTCCTCCTCTACGTCGTTGTGGTGGATTTGCCGACGCACATAGCCCAGATCGC    3900
F  Q  F  L  L  Y  V  V  V  D  L  P  T  H  I  A  Q  I  A

TACCTGGCTGGGCCAGTACCCGCAGTTGCTGTCGGCTGCCCTCACTGGCGTCATCGCCCA    3960
T  W  L  G  Q  Y  P  Q  L  L  S  A  A  L  T  G  V  I  A  H

CCTGGGAGCAATAACTGGTTTGGCGGGCCTATCCGGCCTGAGCGCCATTCCGTCTGCTGC    4020
L  G  A  I  T  G  L  A  G  L  S  G  L  S  A  I  P  S  A  A

GATACCCGCCGTTGTACCGGAGCTGACACCCGTCGCGGCCGCGCCGCCTATGTTGGCGGT    4080
I  P  A  V  V  P  E  L  T  P  V  A  A  A  P  P  M  L  A  V

CGCCGGGGTGGGCCCTGCAGTCGCCGCGCCGGGCATGCTCCCCGCCTCAGCACCCGCACC    4140
A  G  V  G  P  A  V  A  A  P  G  M  L  P  A  S  A  P  A  P

GGCGGCAGCGGCCGGCGCCACCGCAGCCGGCCCGACGCCGCCGGCGACTGGTTTCGGAGG    4200
A  A  A  A  G  A  T  A  A  G  P  T  P  P  A  T  G  F  G  G

GCTTCCCGCCCTACCTGGTCGGCGGTGGCGGCCCAGGAATAGGGTTCGGCTCGGGACAGT    4260
L  P  A  L  P  G  R  R  W  R  P  R  N  R  V  R  L  G  T  V

CGGCCCACGCCAAGGCCGCGGCGTCCGATTCCGCTGCAGCCGAGTCGGCGGCCCAGGCCT    4320
G  P  R  Q  G  R  G  V  R  F  C  S  R  V  G  G  P  G  L

CGGCGCGTGCGCAGGCGCGTGCTGCACGGCGGGGCCGCTCGGCGGCAAGGCACGTGGCCA    4380
G  A  C  A  G  A  C  C  T  A  G  P  L  G  G  K  A  R  G  H

TCGTGACGAATTC                                                   4393
R  D  E  F
```

FIG. 2D

HOMOLOGOUSLY RECOMBINANT SLOW GROWING MYCOBACTERIA AND USES THEREFOR

RELATED APPLICATIONS

This application is a continuation of U.S. Ser. No. 08/095,734, filed Jul. 22, 1993, now U.S. Pat. No. 5,807,723, which is a Continuation-in-Part (CIP) of U.S. Ser. No. 07/711,334, filed Jun. 6, 1991, now abandoned, which is a CIP of U.S. Ser. No. 07/367,894, filed Jun. 19, 1989, now abandoned, which is a CIP of U.S. Ser. No. 07/361,944, filed Jun. 5, 1989, now U.S. Pat. No. 5,504,005, which is a CIP of U.S. Ser. No. 07/223,089, filed Jul. 22, 1988, now abandoned, and of U.S. Ser. No. 07/216,390, filed Jul. 7, 1988, now abandoned. This application is also related to U.S. Ser. No. 07/163,546, filed Mar. 3, 1988, now abandoned, U.S. Ser. No. 07/020,451, filed Mar. 2, 1987, now abandoned, International Application No. PCT/US94/08267, filed Jul. 22, 1994, International Application No. PCT/US90/0345 1, filed Jun. 18, 1990, International Application No. PCT/US89/02962, filed Jul. 7, 1989, and International Application No. PCT/US88/00614, filed Feb. 29, 1988. All of the above applications are incorporated herein by reference in their entirety.

BACKGROUND OF THE INVENTION

The World Health Organization estimates that one in three human beings is believed to be infected with *Mycobacterium tuberculosis* (Styblo, K., *Reviews of Infectious Diseases. Vol. II*, Suppl. 2, March–April, 1989; Bloom and Murray, *Science* 257:1055–1067, 1992). Over the past decade, there has been a recent resurgence in the incidence of tuberculosis in developed countries that has coincided with the AIDS epidemic (Snider and Roper, *N. England J. Med.* 326:703–705 (1992)). Because of their impact as major human pathogens and as a result of their profound immunostimulatry properties, mycobacteria have long been intensively studied. In the early 1900s, an attenuated mycobacterium, *Mycobacerium(M.) bovis* Bacille Calmette-Guerin (*M. bovis* BCG or BCG), was isolated for use as a vaccine against tuberculosis (Calmette et al. *Acad. Natl. Med.* (*Paris*), 91:787–796, 1924; reviewed in Collins, F. M., *Bacterial Vaccines* (R. Germanier, ed.), Academic Press, pp. 373–418, 1984). Although the efficacy of this vaccine against tuberculosis varied considerably in different trials, and the reasons for its variable efficacy have yet to be resolved, BCG is among the most widely used human vaccines (Luelmo, F., *Am. Rev. Respir. Dis.* 125:70–72, 1982; Fine, P. E. M., *Reviews of Infectious Diseases II* (*supp.* 2), 5353–5359, 1989).

The recent application of molecular biological technology to the study of mycobacteria has led to the identification of many of the major antigens that are targets of the immune response to infection by mycobacteria (Kaufmann, S. H. E., *Immunol. Today* 11:129–136, 1990; Young, R. A., *Ann. Rev. Immunol.* 8:401–420, 1990; Young et al., *Academic Press Ltd.*, London, pp. 1–35, 1990; Young et al., *Mol. Microbiol.* 6:133–145, 1992)) and to an improved understanding of the molecular mechanisms involved in resistance to antimycobacterial antibiotics (Zhang et al., *Nature* 358:591–593, 1992; Telenti et al., *Lancet* 341:647–650, 1993). The development of tools that permit molecular genetic manipulation of mycobacteria has also allowed the construction of recombinant BCG vaccine vehicles (Snapper et al., *Proc. Natl. Acad. Sci. USA* 85:6987–6991, 1988; Husson et al., *J. Bacteriol.* 172:519–524, 1990; Martin et al., *B. Nature* 345:739–743, 1990; Snapper et al., *Mol. Microbiol.* 4:1911–1919, 1990; Aldovini and Young, *Nature* 351:479–482, 1991; Jacobs et al., *Methods Enzymol.* 204:537–555, 1991; Lee et al., *Proc. Natl. Acad. Sci. USA* 88:3111–3115, 1991; Stover et al., *Nature* 351: 456–460, 1991; Winter et al., *Gene* 109:47–54, 1991; Donnelly-Wu et al., *Mol. Microbiol.* 7:407–417, 1993)). Genome mapping and sequencing projects are providing valuable information about the *M. tuberculosis* and *M. leprae* genomes that will facilitate further study of the biology of these pathogens (Eiglmeier et al., *Mol. Microbiol.*, in press, 1993; Young and Cole, *J. Bacteriol.* 175:1–6, 1993).

Despite these advances, there are two serious limitations to our ability to manipulate these organisms genetically. First, very few mycobacterial genes that can be used as genetic markers have been isolated (Donnelly-Wu et al., *Mol. Microbiol.* 7:407–417, 1993)). In addition, investigators have failed to obtain homologous recombination in slow growing mycobacteria, such as *M. tuberculosis* and *M. bovis* BCG (Kalpana et al., *Proc. Natl. Acad. Sci. USA* 88:5433–5447, 1991; Young and Cole, *J. Bacteriol.* 175:1–6, 1993)), although homologous recombination has been accomplished in the fast growing *Mycobacterium smeamatis* (Husson et al., *J. Bacteriol.* 172: 519–524, 1990)).

SUMMARY OF THE INVENTION

Described herein is a method of transforming slow-growing mycobacteria, such as *M. bovis* BCG, *M. leprae, M. tuberculosis M. avium, M. intracellulare* and *M. africanum*; a method of manipulating genomic DNA of slow-growing mycobacteria through homologous recombination; a method of producing homologously recombinant (HR) slow-growing mycobacteria in which heterologous DNA is integrated into the genomic DNA at a homologous locus; homologously recombinant (HR) slow-growing mycobacteria having heterologous DNA integrated into their genomic DNA at a homologous locus; and mycobacterial DNA useful as a genetic marker.

Applicants have succeeded in introducing heterologous DNA into (i.e., transforming) slow-growing mycobacteria through the use of electroporation in water (rather than in buffer). In the present method of transforming slow-growing mycobacteria, heterologous DNA (such as linear DNA or plasmid DNA) and slow-growing mycobacteria (e.g., *M. bovis* BCG, *M. leprae, M. tuberculosis M. avium, M. intracellulare* and *M. africanum*) are combined and the resulting combination is subjected to electroporation at an appropriate potential and capacitance for sufficient time for the heterologous DNA to enter the slow growing mycobacteria, resulting in the production of transformed mycobacteria containing the heterologous DNA. In one embodiment, heterologous DNA and *M. bovis* BCG are combined and subjected to electroporation in water. In a particular embodiment, the *M. bovis* BCG-heterologous DNA combination is subjected to electroporation in water at settings of approximately 2.5 kV potential and approximately 25 μF capacitance. Optionally, prior to harvest, cells to be transformed are exposed to glycine (such as by adding 1–2% glycine to culture medium in which the slow-grow mycobacteria are growing) in order to enhance or improve transformation efficiencies. In one embodiment, 1.5% glycine is added to the culture medium 24 hours prior to harvesting of the cells, which are then combined with heterologous DNA to be introduced into the slow-growing mycobacteria. The resulting combination is subjected to electroporation, preferably in water, as described above.

In a further embodiment of the method of transforming slow growing mycobacteria, cultures of the cells are maintained in (continuously propagated in) mid-log growth, in order to increase the fraction of cells which are undergoing DNA synthesis (and which, thus, are competent to take up heterologous DNA). Cultures of cells maintained in log-phase growth are subjected to electroporation, preferably in water and, as a result, are transformed with the heterologous DNA. As described above, efficiency of transformation can be increased by exposing the slow-growing mycobacteria to glycine prior to electroporation. Thus, in this embodiment, slow-growing mycobacteria in log-phase growth are combined with heterologous DNA (e.g., plasmid DNA, linearized DNA) to be introduced into the slow-growing mycobacteria. The resulting combination is subjected to electroporation (preferably in water), under conditions (potential and capacitance settings and sufficient time) appropriate for transformation of the cells. Optionally, prior to electroporation, the log-phase cells are exposed to glycine (e.g., approximately 1–2% glycine added to culture medium) in order to enhance transformation efficiency.

Heterologous DNA introduced into slow-growing mycobacteria is DNA from any source other than the recipient mycobacterium. It can be homologous to DNA present in the recipient mycobacterial genomic DNA, nonhomologous or both. DNA which is homologous to mycobacterial genomic DNA is introduced into the genomic DNA by homologous recombination or integration. Alternatively, the heterologous DNA introduced by the present method can be nonhomologous and, thus, enter mycobacterial genomic DNA by random integration events or remain extrachromosomal (unintegrated) after it enters the mycobacterium. In addition, in one embodiment of the present method, nonhomologous DNA linked to or inserted within DNA homologous to genomic DNA of the recipient mycobacterium is introduced into genomic DNA of the recipient mycobacterium as a result of homologous recombination which occurs between genomic DNA and the homologous DNA to which the nonhomologous DNA is linked (or in which it is inserted). For example, as described herein, a mycobacterial gene which encodes a genetic marker has been identified and isolated and used to target homologous integration of heterologous DNA (DNA homologous to genomic DNA of the mycobacterial recipient, alone or in conjunction with DNA not homologous to genomic DNA of recipient mycobacteria) into genomic DNA of a slow-growing mycobacterium. Specifically, the *M. bovis* BCG gene encoding orotidine-5-monophosphate decarboxylase (OMP DCase) (uraA) has been isolated, as has DNA flanking QMP DCase. The OMP DCase gene and the flanking DNA have been sequenced. The mycobacterial DNA containing the uraA locus, modified to contain heterologous DNA (a selectable marker gene) has been used to carry out integration of the heterologous DNA (the mycobacterial DNA and the selectable marker gene) into mycobacterial genomic DNA, resulting in production of homologously recombinant mycobacteria containing the heterologous DNA of a homologous locus. Specifically, *M. bovis* BCG DNA containing the uraA locus and flanking sequences was modified to replace the OMP DCase coding sequence with the Kanr selectable marker gene (aph). The resulting construct, which included approximately 1.5 kb uraA flanking sequences on each side of the selectable marker gene, was transformed into *M. bovis* BCG, using the method described above. *M. bovis* BCG cultures in mid-log growth were subjected to electroporation in water, resulting in transformation of cells with the construct. Transformants were selected for further study, which showed that all transformants assessed contained vector DNA integrated into the genome and that in some of the transformants, the transforming DNA had integrated at the homologous genomic locus. Thus, heterologous DNA of interest has been introduced into genomic DNA of slow-growing mycobacteria through homologous recombination, to produce homologously recombinant slow-growing mycobacteria in which the heterologous DNA is integrated into the homologous genomic locus (a genomic locus homologous to at least a portion of the heterologous DNA).

Heterologous DNA which includes DNA homologous to genomic DNA of the recipient mycobacterium (homologous DNA) and DNA which is not homologous to genomic DNA of the recipient mycobacterium (nonhomologous DNA) can be introduced into (transformed into) slow growing mycobacterium by the present method for several purposes. As described herein, heterologous nonhomologous DNA encoding a product to be expressed by the resulting homologously recombinant slow-growing mycobacterium has been introduced into mycobacterial genomic DNA at a locus homologous with additional sequences to which the nonhomologous DNA is linked. In this embodiment, the DNA construct transformed into recipient slow-growing mycobacteria comprises homologous DNA, which directs or targets introduction of the heterologous DNA into the homologous locus of the mycobacterial genome, and nonhomologous DNA, which is expressed in transformed homologously recombinant mycobacteria. In this embodiment, the nonhomologous DNA is introduced into mycobacterial genomic DNA in such a manner that it is added to the genomic DNA or replaces genomic DNA. In a second embodiment, heterologous DNA integrated into genomic DNA is not expressed in the recipient cells. In this embodiment, the DNA construct includes homologous DNA for targeting into a homologous genomic locus and DNA which acts to knock out (inactivate) or activate a resident mycobacterial gene. In the case of inactivation, the mycobacterial gene is "knocked out", in the sense that it is rendered inactive by addition of DNA whose presence interferes with its ability to function, by removal or replacement of sequences necessary for it to be functional or by its complete removal from the mycobacterial genome. In the case of activation, the heterologous DNA integrated into the genomic DNA turns on or enhances expression of a mycobacterial gene, such as by introducing a heterologous promoter which controls the mycobacterial gene expression. In the embodiment in which heterologous DNA affects expression of an endogenous mycobacterial gene, the homologous DNA can serve both functions (i.e., the targeting and inactivation/activating functions); if that is the case, the DNA construct includes only homologous DNA. Alternatively, the DNA construct can include homologous DNA (for targeting purposes) and nonhomologous DNA (for altering function of the mycobacterial gene).

Homologously recombinant slow-growing mycobacteria of the present invention are useful, for example, as vehicles in which proteins encoded by the heterologous nonhomologous DNA are expressed. They are useful as vaccines, which express a polypeptide or a protein of interest (or more than one polypeptide or protein), such as an antigen or antigens of one or more pathogens against which protection is desired (e.g., to prevent or treat a disease or condition caused by the pathogen). Pathogens of interest include viruses, retroviruses, bacteria, mycobacteria, other microorganisms, organisms or substances (e.g., toxins or toxoids) which cause a disease or condition to be prevented, treated or reversed. The homologously recombinant slow-growing bacteria can also be used to express enzymes, immunopotentiators, lymphokines, pharmacologic agents, antitumor agents (e.g., cytokines), or stress proteins (useful for evoking or enhancing an immune response or inducing tolerance in an autoimmune disease). For example, homologously recombinant slow-growing mycobacteria of the present invention can express polypeptides or proteins which are growth inhibitors or are cytocidal for tumor cells (e.g., interferon α, β or γ, interleukins 1–7, tumor necrosis factor (TNF) α or β) and, thus, are useful for treating certain human cancers (e.g., bladder cancers, melanomas). Homologously recombinant slow-growing mycobacteria of the present invention are also useful vehicles to elicit protective immunity in a host, such as a human or other vertebrate. They can be used to produce humoral antibody immunity, cellular immunity and/or mucosal or secretory immunity. The antigens expressed by the homologously recombinant slow-growing mycobacteria, useful as vaccines or as diagnostic reagents, are also the subject of the present invention. In addition, homologously recombinant slow-growing mycobacteria of the present invention are useful as vaccines in which the heterologous DNA introduced through homologous integration is not itself expressed, but acts to knock out a mycobacterial gene necessary for pathogenicity of the slow-growing mycobacterium or its growth in vivo. Such homologously recombinant slow-growing mycobacteria are useful as vaccines to provide protection against diseases caused by the corresponding wild-type mycobacterium or as a vaccine vehicle which contains a gene(s) encoding an antigen(s) of a different pathogen(s) (e.g., as a vaccine to provide protection against an organism other than the corresponding wild-type mycobacterium or against a toxin or toxoid).

The vaccine of the present invention has important advantages over presently available vaccines. For example, mycobacteria have adjuvant properties; they stimulate a recipient's immune system to respond to other antigens with great effectiveness. In addition, the mycobacterium stimulates long-term memory or immunity. This means that a single (one time) inoculation can be used to produce long-term sensitization to protein antigens. Long-lasting T cell memory, which stimulates secondary antibody response neutralizing to the infectious agent or toxic. This is particularly useful, for example, against tetanus and diphtheria toxins, pertussis, malaria, influenza, herpes viruses and snake venoms.

BCG in particular has important advantages as a vaccine vehicle. For example, it can be used repeatedly in an individual and has had a very low incidence of adverse effects. In addition, BCG, as well as other mycobacteria, have a large genome (approximately $3\times10^6$ bp in length). As a result, a large amount of heterologous DNA can be accommodated within (incorporated into) the mycobacterial genome, which means that a large gene or multiple genes (e.g., DNA encoding antigens for more than one pathogen) can be inserted into genomic DNA, such as by homologous recombination.

Figure 1:
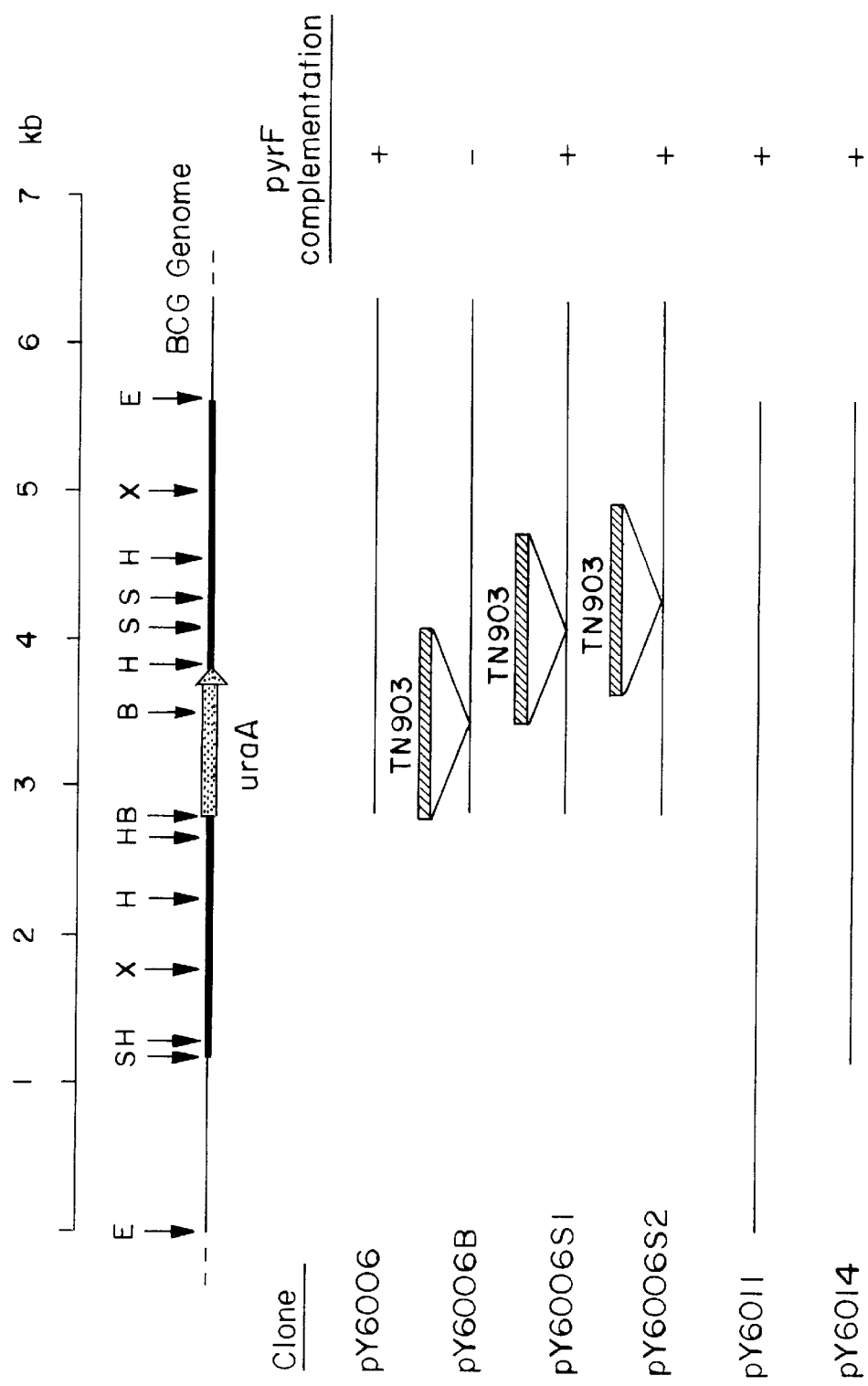
FIG. 1 is a structural and functional map of the *M. bovis* BCG uraA locus, in which a restriction map of the uraA locus and the recombinant insert DNAs for several plasmids used to study this region are depicted. The relative positions of the BCG uraA gene and the portions of other genes identified are summarized graphically and the ability of each recombinant to complement the *E. coli* pyrF mutant is indicated.

FIGS. 2A–2D is the nucleic acid sequence of the BCG uraA locus (Seq ID No. 1) and the predicted protein products (Seq ID No. 2).

FIG. 3 is a schematic representation of integration by homologous recombination in BCG. The uraA locus in wild-type BCG (top), the transforming DNA (middle) and a BCG transformant in which the transforming DNA fragment has integrated via homologous recombination (bottom) are represented.

FIG. 4 is a schematic representation of the Southern analysis of the BCG transformant represented in FIG. 3.

FIG. 5 shows the results of Southern blot analysis of genomic DNA isolated from wild-type BCG (WT) and a BCG transformant (6015–9). The positions of DNA markers are indicated to the right and the apparent size of each of the hybridizing DNA bands is indicated to the left.

DETAILED DESCRIPTION OF THE INVENTION

As described herein, Applicants have demonstrated introduction of heterologous DNA into slow-growing mycobacteria (transformation of heterologous DNA into slow-growing mycobacteria) and incorporation of heterologous DNA at a homologous locus in genomic DNA of slow-growing mycobacterial (integration of heterologous DNA into the genomic DNA through homologous recombination). As a result, they have produced homologously recombinant slowgrowing mycobacteria having heterologous DNA integrated at a homologous locus in their genomic DNA. In particular, as described herein, Applicants have introduced heterologous DNA into *M. bovis* BCG (BCG) and demonstrated that it is present in the resulting homologously recombinant BCG at a genomic location homologous with sequences present in the DNA construct transformed into the BCG. The DNA construct introduced into BCG by the method described herein included heterologous DNA containing the uraA locus (homologous DNA) and nonhomologous DNA (a selectable marker gene); the heterologous homologous DNA flanked the nonhomologous DNA in the construct. Both the heterologous homologous DNA and the heterologous nonhomologous DNA in the DNA construct were shown to have integrated into the genome of the recipient mycobacterial cells at a homologous locus (a genomic locus homologous with the DNA including and/or flanked by the homologous DNA in the DNA construct).

As a result of the work described herein, a method of transforming slow growing mycobacteria, a method of introducing heterologous DNA into genomic DNA of a slow growing mycobacterium through integration at a homologous locus, DNA constructs useful in the method of introducing heterologous DNA into a homologous locus in genomic DNA of a slow growing mycobacteria, homologously recombinant slow growing mycobacteria which contain heterologous DNA at a homologous locus in their genomic DNA, a BCG gene encoding orotidine-5'-monophosphate decarboxylase (BCG OMP DCase) and homologously recombinant slow growing mycobacteria useful as vaccines are available. The following is a description of the present method, DNA constructs and vaccines, as well as the isolated BCG OMP DCase gene and its use.

The present invention includes an improved method of transforming slow growing mycobacteria. In the present method, slow growing mycobacteria are subjected to electroporation in water, preferably after exposure to (culturing in the presence of) glycine prior to electroporation and preferably also while they are in mid-log growth. Slow growing mycobacteria to be transformed with heterologous DNA are combined with the heterologous DNA (which can be plasmid/circular DNA or linear DNA) in water. The resulting combination is subjected to electroporation under conditions (e.g., potential, capacitance and time) sufficient for entry of the heterologous DNA into the slow growing mycobacteria. Electroporation is carried out at approximately 2 to 2.5 kV potential and approximately 1 to 125 $\mu$F capacitance for approximately 4 to 40 milliseconds. In a specific embodiment, slow growing mycobacterial cells are electroporated in water at approximately 2.5 kV potential and approximately 25 $\mu$F capacitance for 5–6 milliseconds. In a further embodiment, slow growing mycobacteria to be transformed are exposed to glycine (e.g., 1 to 2% glycine) by addition of glycine to culture medium prior to harvest of the cells. In a particular embodiment, slow growing mycobacteria are exposed to 1.5% glycine, which is added to culture medium, for approximately 24 hours prior to harvest of the cells for transformation. In another embodiment, slow-growing mycobacteria are in mid-log growth when they are transformed. The cells can also have been exposed to glycine, as described above, prior to electroporation, although that is not necessary. The mid-log slow growing mycobacteria are combined with heterologous DNA to be introduced into them and subjected to elecroporation in water, as described above, resulting in transformation of the heterologous DNA into slow growing mycobacteria in the combination.

The heterologous DNA introduced into slow growing mycobacteria by the present method is DNA obtained from any source other than the mycobacterium into which it is being introduced. It can be of viral, bacterial, mycobacterial, invertebrate or vertebrate (including human and other mammalian) origin, can be obtained from other organisms, such as parasites, or can be produced to have the same nucleic acid sequence as the DNA in its naturally occurring source. Alternatively, it can be modified DNA. The DNA introduced can be plasmid (circular) DNA or linear DNA. The heterologous DNA contains DNA homologous to a locus in genomic DNA of the recipient slow growing mycobacteria, DNA nonhomologous to a locus in genomic DNA of the recipient cells or both. It is possible to combine slow growing mycobacteria and a DNA construct in which the heterologous DNA is only nonhomologous DNA and carry out the present method of transformation, if the goal is to transform slow growing mycobacteria with greater efficiency than is possible with existing methods. Heterologous DNA introduced in this manner will integrate randomly into genomic DNA.

In order to produce homologously recombinant slow growing mycobacteria through homologous integration between mycobacterial genomic DNA and heterologous DNA, the DNA construct must include sufficient DNA homologous with mycobacterial DNA to cause integration of the construct into a homologous genomic locus. If only homologous DNA is present in the DNA construct used (e.g., in a construct introduced in order to knock out or activate endogenous mycobacterial DNA), at least 400 bp of homologous DNA will generally be used. If the DNA construct includes homologous DNA (for directing or targeting introduction into mycobacterial genomic DNA) and nonhomologous DNA (e.g., DNA encoding a product to be expressed in homologously recombinant slow growing mycobacteria), there is homologous DNA on both sides of (flanking both ends of) the nonhomologous DNA. In general, there will be at least approximately 250 bp of homologous DNA on each side of the nonhomologous DNA, although shorter flanking homologous sequences can be used, provided that they are of sufficient length to undergo homologous recombination with genomic sequences, resulting in their introduction into mycobacterial genomic DNA (alone or in conjunction with nonhomologous DNA with which the homologous DNA is present in the DNA construct). In the embodiment described in the examples, 1.5 kb of homologous DNA (1.5 kb of uraA flanking sequence) has been shown to result in homologous integration, along with nonhomologous DNA, into the uraA locus of *M. bovis* BCG.

The homologous DNA present in the DNA construct can be any DNA homologous to DNA present in genomic DNA of the recipient slow growing mycobacterium. Specifically described herein is the isolation and sequencing of the *M. bovis* BCG OMP DCase gene (uraa) and its use to introduce heterologous nonhomologous DNA into *M. bovis* BCG genomic DNA at a homologous locus. As described in the examples, a BCG DNA fragment which included the OMP DCase coding sequence was modified to remove the OMP DCase coding sequence and replace it with heterologous nonhomologous DNA encoding a selectable marker gene (i.e., the Kan$^r$ (aph) gene). Specifically, the DNA construct was made by removing the OMP Dcase coding sequence from a 4.4 kb BCG DNA fragment containing uraA and replacing it with the Kan$^r$ gene (aph), to produce a DNA fragment in which the selectable marker gene is flanked by 1.5 kb uraA DNA (to direct homologous recombination or integration of the homologous DNA and, along with it, the nonhomologous DNA into mycobacterial genomic DNA). All or a portion of the OMP DCase gene can be used, with similar modifications, as a component of a DNA construct including other heterologous nonhomologous DNA to be introduced into *M. bovis* BCG genomic DNA at the uraA locus. Alternatively, other *M. bovis* BCG genes can be used as the heterologous homologous component of a DNA construct useful for introducing heterologous nonhomologous DNA into the mycobacterium. Similarly, DNA from other slow growing mycobacteria (e.g., *M. leprae, M. tuberculosis, M. avium, M. africanum*) can be incorporated into a DNA construct to be used for homologous recombination in the respective slow growing mycobacteria.

The heterologous nonhomologous DNA in the DNA construct introduced into slow growing mycobacteria by the present method can be any DNA which is expressed in the slow-growing mycobacteria or which is not expressed in the recipient mycobacteria but alters mycobacterial protein expression or function. For example, the heterologous nonhomologous DNA can be DNA encoding an antigen(s) of a pathogen or pathogens. A pathogen is any virus, microorganism, other organism or substance (e.g., toxins, toxoids) which causes a disease or undesirable condition. Homologously recombinant slow growing mycobacteria which express a protein antigen(s) from malaria sporozoites, malaria merozoites, diphtheria toxoid, tetanus toxoid, Leishmania, Salmonella, *M. africanum, M. intracellulare, M. avium*, treponema, pertussis, herpes virus, measles virus, mumps, Shigella, Neisseria, Borrelia, rabies, poliovirus, human immunodeficiency virus (HIV), Simian immunodeficiency virus (SIV), snake venom, insect venom or vibrio cholera can be produced using the method of the present invention. Homologously recombinant *M. bovis* BCG, which, in a nonhomologously recombinant form, has long been successfully administered as a vaccine in humans can be used. The DNA encoding the protein antigen(s) can be obtained from sources in which it naturally occurs or can be produced through known recombinant techniques or known chemical synthetic methods. For example, the DNA can be produced by genetic engineering methods, such as cloning or by the polymerase chain reaction (PCR).

A multipurpose or multifunctional vaccine (one which contains and expresses heterologous DNA encoding antigens from more than one pathogen) can be produced by the present method. In this embodiment, one or more DNA constructs are used to introduce heterologous homologous DNA and heterologous nonhomologous DNA (DNA encoding an antigen against which protection is desired) into the slow growing mycobacterium. If one construct is used, it includes DNA encoding the antigens of interest, flanked by homologous DNA sufficient for introduction of the heterologous DNA into a homologous locus in the mycobacterium. More than one construct can be used; in this case, each includes homologous DNA and nonhomologous DNA encoding an antigen of interest. A multifunctional vaccine of the present invention can be homologously recombinant BCG which contains, within its genomic DNA, a gene encoding an antigen for M. leprae, a gene encoding an antigen for M. tuberculosis, a gene encoding an antigen for malaria and a gene encoding an antigen for Leishmania; these sequences are flanked by heterologous sequences homologous with BCG DNA and are introduced into the BCG genome by homologous integration.

It is not necessary that heterologous nonhomologous DNA be expressed by homologously recombinant slow growing mycobacteria of the present invention or even that there be heterologous nonhomologous DNA present. For example, in one embodiment, heterologous nonhomologous DNA is incorporated into genomic DNA of slow growing mycobacteria for the purpose of inactivating an endogenous mycobacterial gene, such as a gene necessary for the pathogenicity of the mycobacterium. Any gene involved in metabolism necessary for pathogenicity of the slow growing mycobacterium (or for its growth in humans or other animals) but whose absence (e.g., from being knocked out) does not prevent it from being cultured can be targeted for inactivation. For example, the AROA gene of M. tuberculosis can be inactivated. In another embodiment, heterologous nonhomologous DNA is introduced in order to activate or turn on an endogenous mycobacterial gene. In either case, the heterologous nonhomologous DNA need not be expressed.

Heterologous DNA can be homologous DNA only; it is not necessary that heterologous nonhomologous DNA be present. For example, homologous DNA can be introduced into an endogenous mycobacterial gene (such as one essential for the pathogenicity of a slow growing mycobacterium) in order to disrupt or inactivate that gene. This is particularly useful in those embodiments in which an attenuated or disabled mycobacterium is desired, such as for use as a vaccine to elicit an immune response against the mycobacterium itself or as a vehicle to be used in a similar manner to that in which homologously recombinant BCG can be used (to express antigens of other pathogens).

Homologously recombinant slow growing mycobacteria of the present invention can be administered by known methods and a variety of routes (e.g., intradermally, intramuscularly, intravenously). They are useful as vehicles in which the heterologous nonhomologous DNA is expressed and as modified slow grow mycobacteria (e.g., mycobacteria with reduced or abolished pathogenicity) which are disabled or attenuated and, thus, useful as vaccines.

The present invention will now be illustrated by the following examples, which are not to be considered limited in any way.

MATERIALS AND METHODS

Strains and plasmids. M. bovis BCG used for DNA isolation and subsequent construction of the recombinant BCG plasmid and λgt11 libraries was the Montreal Strain, ATCC #35735. M. bovis BCG was grown in Middlebrook 7H9 media, supplemented with 0.05% Tween 80, as described in Aldovini and Young, Nature 351:479–482, (1991). E. coli strain Y1107 (pyrF::Mu trpam laczam hsdR-m+su-) was obtained from D. Botstein. Plasmids were propagated in the E. coli strain DH5a from Bethesda Research Laboratories. E. coli cultures used for plasmid selection were grown in Luria Bertani broth or agar with 50 µg/ml ampicillin. Phage M13 used for the production of single stranded DNA were propagated in E. coli strain JM101 from New England BioLabs. JM101 was grown in YT medium (Maniatis). Genomic libraries were generated using pUC19 from Bethesda Research Laboratories. Plasmid pY6002 (Husson et al., J. Bacteriol., 172:519–524 1990) was the source of the 1.3 kb BamHI DNA fragment containing the aminoglycoside phosphotransferase gene aph.

Enzymes. Klenow fragment of E. coli DNA polymerase was supplied by Promega. T7 polymerase, and Taq polymerase (Sequenase and Taquence) were provided by United States Biochemical.

Recombinant DNA library construction. To isolate BCG DNA, cells were harvested by centrifugation, washed, and resuspended in 50 mM Tris (pH 8.0), 10 mM EDTA, 10% sucrose, and 0.5 mg/ml lysozyme, and incubated at 37 degrees for one hour. EDTA was then added to 1%, and the mixture was incubated at room temperature for 15 minutes. Three phenol/chloroform extractions were performed, followed by RNase treatment, phenol/chloroform extraction, chloroform extraction and ethanol precipitation. The DNA was then resuspended in TE buffer, (10 mM Tris pH 7.5, imM EDTA).

To construct the plasmid library, the DNA was subjected to partial digestion with Sau3A and DNA fragments of 2–6 kb were isolated by agarose gel electrophoresis onto DE81 paper and eluted in buffer containing 10 mM Tris, HC1, 1M NaCl and 1 mM EDTA. The DNA fragments were then phenol-chloroform extracted, ethanol precipitated and ligated into BamH1 digested, calf-intestinal phosphatase treated pUC19 plasmid vector. E. coli cells were transformed with the ligated mixture, and approximately $4 \times 10^5$ recombinants were obtained. Plasmid DNA was obtained from the pool of transformed colonies using an alkaline lysis method.

The λgt11 library was constructed using a procedure described by Young. (Young, R. A., et al., Proc. Natl. Acad. Sci., USA, 82:2583–2587 (1985)). Briefly, BCG genomic DNA was subjected to random partial digestion with DNase I, EcoRI linkers were added to the digestion products, and DNA fragments of 4–8 kb were isolated by agarose gel electrophoresis and electroelution. The DNA fragments were then ethanol precipitated and ligated into EcoRI-digested λgt11 arms. The ligation mixture was packaged into λ heads and the packaging mixture was used to infect E. coli. Approximately $5 \times 10^6$ recombinants were obtained.

EXAMPLE 1.

Isolation of BCG OMP DCase gene by complementation and plasmid DNA manipulation. The BCG recombinant library was used to transform the E. coli strain Y1107. Twenty-one transformants capable of growing in the absence of uracil were isolated, of which six were chosen for further evaluation by restriction analysis. Plasmid DNA was isolated by alkaline lysis from cells grown in liquid culture, and restriction analysis indicated that all of these plasmids contained the same or very similar insert DNAs. One of these clones (pY6006) was used for further study (see FIG. 1). A 0.6 kb BamHI DNA fragment from pY6006 was used to screen the λgt11 library, leading to the isolation of phage Y3030. This phage carries a 5.6 kb EcoRI BCG DNA insert containing the OMP DCase gene. This insert DNA was subcloned into pGEMz(f+) to generate pY6011. The 4.4 kb SacI-EcoRI fragment of the Y3030 insert was subcloned into pUC19 to generate pY6014. Plasmid pY6015 was derived from pY6014 by replacing uraA sequences with the aph gene; a 1.15 kb HincII DNA fragment containing uraA sequences was removed by partial HincII digestion of pY6014 DNA, and it was replaced with a 1.3 kb BamHI fragment containing aph from pY6002 that was blunt-ended with Klenow.

DNA Sequence analysis. The *M. bovis* BCG uraA gene was sequenced from the 4.4 kb SacI-EcoRI fragment of the λgt11 phage Y3030 cloned into M13 in both orientations. The same DNA fragment was subcloned into pUC19 to generate pY6014 for further manipulation. Single strand DNA for sequence analysis was prepared from M13 grown in JM101 (Viera and Messing, *Methods Enzymol.*, 153:3–11 1987). Both DNA strands were sequenced using the dideoxy-method of Sanger (Sanger et al., *Proc. Natl. Acad. Sci. USA* 74:5463–5467, 1977). Mycobacterial DNA has a high GC content, and two different strategies were used to reduce band compression and other artifacts due to high G+C content. A subset of the reactions was carried out using Taq polymerase at high temperature (70° C.). In addition, dGTP and dITP were used in independent sequence reactions (Kimsey and Kaiser, *J. Biol. Chem.* 267:819–824, 1992).

RESULTS

Isolation of the BCG OMP decarboxylase gene by genetic complementation. The complementation strategy employed to isolate the BCG OMP DCase gene was similar to that employed previously to isolate the homologous gene in *M. smegmatis* (Husson et al., *J. Bacteriol.* 172:519–524, 1990). A recombinant library was constructed in the *E. coli* vector pUC19 using size selected BCG genomic DNA fragments from a partial SauIIIA digest. An *E.coli* pyrF mutant strain (Y1107) was transformed with this library and cells were plated on medium lacking uracil to select for uracil prototrophs, and on rich medium containing ampicillin to ascertain the transformation frequency and to estimate the fraction of transformants that were able to complement the *E.coli* pyrF defect. Approximately 0.05% of the cells transformed with the recombinant library became uracil prototrophs. DNA clones were obtained from six colonies able to grow in the absence of uracil, and restriction analysis revealed that these clones contained the same insert DNA. One of these clones, pY6006, was subjected to further study (FIG. 1).

To identify, the portion of the 3.5 kb insert DNA pY6006 that was responsible for complementation, the 1.3-kb BamHI fragment of Tn903, which encodes aminoglycoside transferase (aph), was inserted into several different sites in pY6006 insert DNA, the resultant plasmids were reintroduced into the *E.coli* pyrF mutant strain, and the ability of the new plasmids to complement the mutant phenotype was assessed as before (FIG. 1). One of the three plasmids with insertion mutations, pY6006B, lost the ability to complement the pyrF mutant phenotype, suggesting that sequences necessary for the complementing activity are located in the vicinity of the BamHI site that is disrupted in pY6006B.

Analysis of DNA sequences for the left end of pY6006 insert DNA (as diagrammed in FIG. 1) revealed that the open reading frame of the pUC19 lacZ gene in this plasmid continues uninterrupted into an open reading frame for a polypeptide similar in sequence to OMP decarboxylase proteins. This preliminary data suggested that the left end of pY6006 insert DNA encoded the amino-terminus of the BCG OMP decarboxylase protein.

For later experiments, it was important to have both the OMP decarboxylase gene and a substantial amount of flanking sequences. To obtain genomic DNA that contains both the OMP decarboxylase gene and its flanking sequences, the 0.6 kb BamHI DNA fragment from pY6006 was used to probe a λgt11 library, of *M. bovis* BCG DNA, as the λgt11 library contains insert DNA fragments whose size, on average, is larger (4–8 kb) than the plasmid library used to obtain pY6006. A lambda clone (Y3030) was isolated which contains a 5.6 kb EcoRI DNA insert that overlaps that of pY6006. The 5.6 kb EcoRI DNA fragment, and a 4.4 kb SacI-EcoRI subfragment, were subcloned into plasmid vectors to generate pY6011 and pY6014, respectively (FIG. 1). Both pY6011 and pY6014 were able to complement the defect of the *E.coli* pyrF mutant strain Y1107.

Sequence of the BCG OMP decarboxylase gene and flanking DNA. DNA fragments, from phage Y3030 insert DNA were subcloned into M13 vectors and subjected to sequence analysis. Sequences were determined for both DNA strands, and most of the sequence reactions were duplicated with ITP replacing GTP to minimize artifacts due to the GC-rich nature of mycobacterial DNA. FIGS. 2A–2D shows the sequences obtained for the BCG OMP decarboxylase gene (uraA) and for flanking DNA. The predicted BCG OMP decarboxylase protein sequence is 274 amino acids long, similar in size to other OMP decarboxylase proteins. When the BCG decarboxylase protein sequence was used to screen the available databases for similar sequences, the results revealed that the BCG protein is closely related to the *Myxococcus xanthus* OMP DCase (Kirnsey and Kaiser, *J. Biol. Chem.* 267:819–824, 1992) and more distantly related to the other known prokaryotic and eukaryotic OMP DCases. Comparison of the BCG and *M. xanthus* OMP decarboxylases reveals that 40% of the amino acid residues are identical. In contrast, only 17% of the residues of the BCG and *E.coli* proteins and 22% of the amino acids of the *M. xanthus* and *E.coli* proteins are identical, although there are a substantial number of conservative amino acid substitutions among these proteins. The relationship of *M. xanthus* OMP decarboxylase to homologues in other prokaryotes and in eukaryotes was recently described in some detail (Kimsey and Kaiser, *J. Biol. Chem.* 267:819–824, 1992). This comparative sequence analysis revealed that there are four regions which are more highly conserved, and the predicted BCG OMP decarboxylase also shares this feature with the other homologues. It is interesting to note that *Mycobacteria* and Myxococci both have GC-rich genomes, but this alone does not account for the degree of sequence conservation between the OMP decarboxylases from these two proaryotes; rather, the two genuses appear to be more closely related to one another than either is to the other prokaryotes for which OMP decarboxylase sequence are available.

Further analysis of the BCG genomic DNA sequences revealed that the 1.7 kb sequence upstream of OMP decarboxylase coding sequences contains a single large open reading frame. This open reading frame has no apparent beginning in the cloned DNA fragment, suggesting that it is the coding sequence for the carboxy-terminus of a larger protein. A screen of the sequence database revealed that the 497 amino acid residues of the predicted protein are highly homologous to the carboxyl termini of the large subunit of carbamoyl phosphate synthase. For example, the 497 amino acid carboxy terminus of the putative *M. bovis* BCG protein was 46% identical to the comparable segment of the *E.coli* carbarnoyl phosphate synthase subunit, which is encoded by the carB gene (Nyunoya and Lusty, *Proc. Natl. Acad. Sci. USA* 80:4629–4633, 1983). Thus, the BCG carB gene appears to be located just upstream of uraA. This is interesting because both carbamoyl phosphate synthase and OMP decarboxylase are involved in pyrimidine biosynthesis. Carbamoyl phosphate synthase catalyzes the first reaction in pyrimidine biosynthesis, the production of carbamoyl phosphate, while OMP decarboxylase catalyzes the last step in the biosynthesis of UMP.

Analysis of BCG DNA sequences downstream of the uraA gene revealed a single large open reading frame that continues through the right end of the sequenced DNA fragment. This open reading frame predicts a protein of 501 amino acids. A search of the computer database revealed that the protein predicted by this ORF is similar to previously described proteins from *M. tuberculosis* and *M. leprae*. The predicted BCG protein is similar to a putative *M. tuberculosis* antigen encoded downstream of the gene for the 65 kDa antigen (Shinnick, T. M., *J. Bacteriol.* 169:1080–1088, 1987) and to a *M. leprae* antigen that may be an integral membrane protein (Vega-Lopez et al., *Infect. Immun.* 61:2145–2154, 1993).

Southern analysis with whole genomic DNA revealed that there is a single copy of the uraA gene and flanking DNA in the BCG genome (see below). The relative positions of the BCG uraA gene and the portions of other genes identified through sequence analysis are summarized graphically in FIG. 1. The position of OMP decarboxylase sequences is consistent with the genetic analysis described above. The aph insertion mutations in plasmid pY6006 that adversely affected complementation of the *E. coli* OMP decarboxylase mutant occurred within OMP decarboxylase coding sequences. Conversely, the aph insertion mutations that did not affect complementation of the *E. coli* OMP decarboxylase mutant occurred outside of the BCG OMP decarboxylase coding sequences.

EXAMPLE 2

BCG transformation. BCG Pasteur (ATCC) was grown in log phase to an $OD_{600}$ of 0.5 in Middlebrook medium. BCG cells were harvested by centrifugation and washed twice with PBS (phosphate buffered saline) and resuspended in 1 mM MgCl (pH 7.2), 10% sucrose, 15% glycerol at a concentration of 10 $OD_{600}$ per ml. 0.4 ml of BCG cells was mixed with 2 ug of plasmid DNA and electroporated in a 0.2 cm cuvette. Electroporation settings were 2.5 kV potential and 25 $\mu F$ capacitance. After electroporation, cells were resuspended in 10 ml Middlebrook medium and incubated at 37° C. for 2 hours before plating on Middlebrook agar containing 20 ug/ml kanamycin and, in some experiments, with uracil.

Southern blot analysis. Genomic DNAs from BCG strains were isolated as described above, digested with restiction enzymes, subjected to agarose gel electrophoresis in the presense of ethidium bromide, transferred to nitrocellulose, and probed with DNA labelled with 32P by random priming, all by standard procedure (Ausubel et al., Current protocol in molecular biology (1987). Green Publishing Associates and Wiley Interscience).

Introduction of foreign DNA into the BCG genome. Previous attempts to obtain homologous recombination in *M. bovis* BCG have apparently not been successful (Kalpana et al., *Proc. Natl. Acad. Sci. USA* 88:5433–5447, 1991; Young and Cole, *J. Bacteriol.* 175:1–6, 1993). It is possible that the efficiency of transformation has an influence on the ability to obtain homologous recombination. To maximize the transformation efficiency of BCG, we investigated the effect of adding glycine to the culture medium prior to harvesting cells for electroporation, as the presence of 1.5% glycine can affect the integrity of the cell wall and it seems to improve transformation effeciency in *M. smegmatis* (Mizuguchi and Takunaga, "Spheroplasts of Mycobacteria. 2. Infection of Phage and Its DNA on Glycine Treated Mycobacteria and Spheroplasts", *Med. Biol.*, 77:57 1968). In addition, we compared the efficiency of electroporation of BCG cells in water relative to buffer. The autonomously replicating plasmid pYUB12 (Snapper et al., *Mol. Microbiol.* 4:1911–1919, 1988) was used to determine how these variables affected the relative efficiencies of transformation. The results are summarized in the Table under Experiment 1. Transformation efficiencies were improved substantially by exposing cultures to 1.5% glycine for 24 hours prior to harvest, and by performing the electroporation in water rather than in buffer.

TABLE

BCG Transformation Efficiencies

| Transforming DNA[a] | Glycine Treatment[b] | Electroporation Medium[c] | Transformants/μg DNA | | |
|---|---|---|---|---|---|
| | | | Expt 1 | Expt 2 | Expt 3 |
| pYUB12 | – | Buffer | 50 | — | — |
| pYUB12 | + | Buffer | 250 | — | — |
| pYUB12 | – | Water | 500 | — | — |
| pYUB12 | + | Water | $10^4$ | $10^4$ | $10^5$ |
| None | + | Water | 8 | 6 | 35 |
| p6015(I) | – | Buffer | — | 4 | — |
| p6015(I) | + | Buffer | — | 22 | — |
| p6015(I) | – | Water | — | 39 | — |
| p6015(I) | + | Water | — | 98 | 500 |

[a]The intact autonomously replicating plasmid pYUB12 was used as a control and the linear insert DNA of plasmid pY6015 [pY6015(I)] was used as integrating DNA.
[b]Glycine was added to 1.5% to BCG cultures 24 hours prior to transformation.
[c]The buffer is 1mM MgCl (pH 7.2), 10% sucrose, 15% glycerol.

Figure 3:
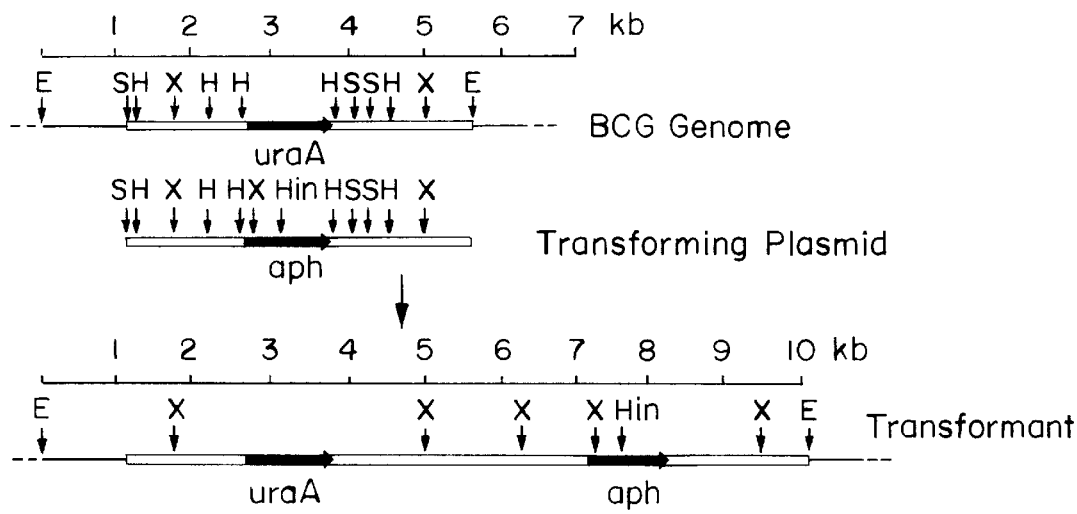
Figure 4:
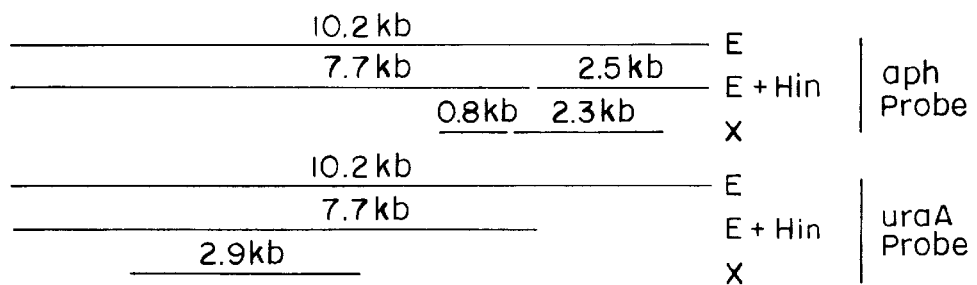
Figure 5:
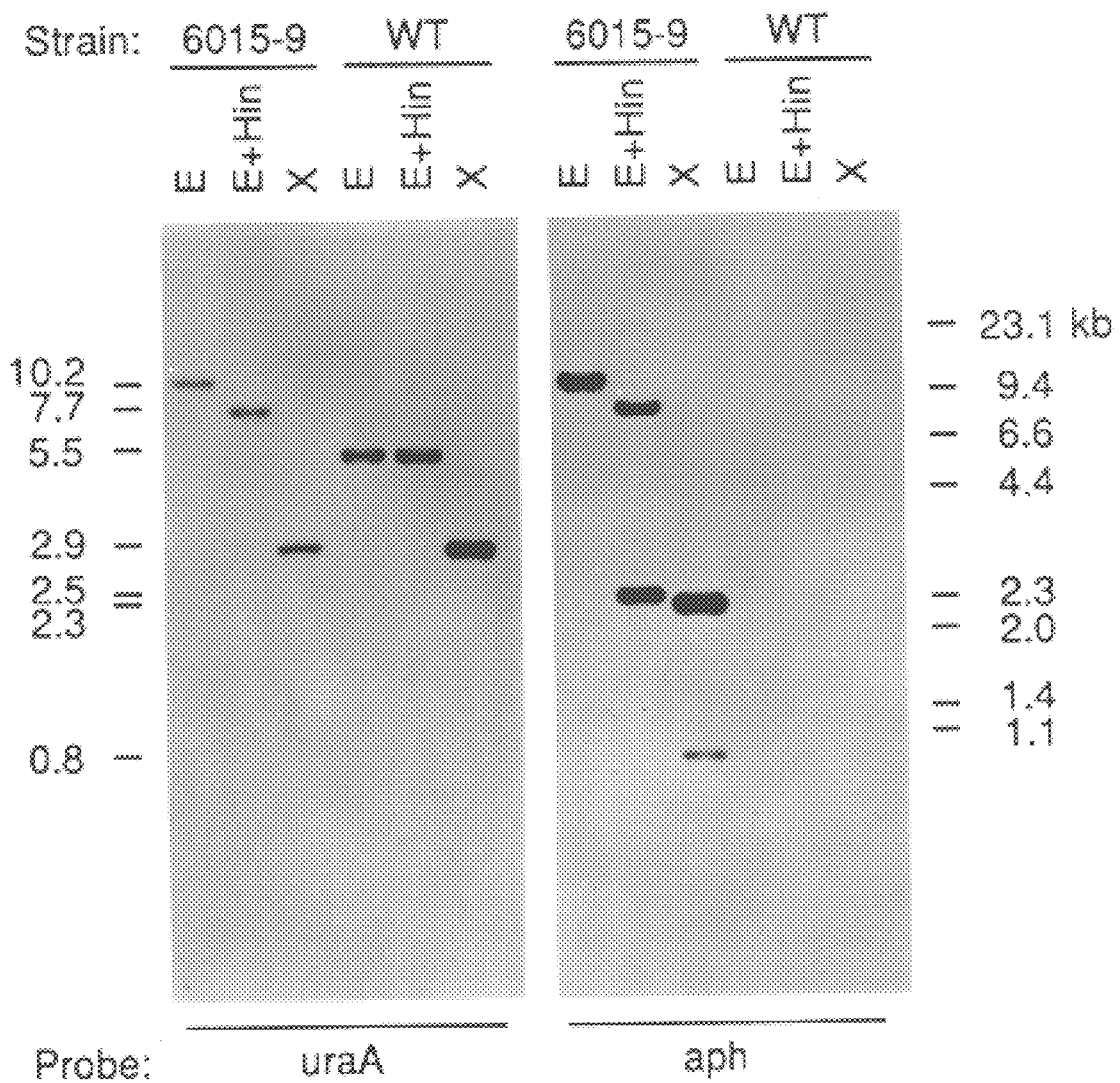

Experiments with linearized DNA molecules in yeast indicate that the ends of linear DNA molecules are recombinogenic; these ends may facilitate homologous integration by invading genomic DNA at homologous sites to initiate recombination (Rothstein, R., *Meth., Enzymol.* 194:281–301 (1988)). The sequenced 4.4 kb BCG DNA fragment containing UraA was used to investigate whether cloned DNA sequences could integrate at the homologous locus in *M. bovis* BCG. To mark the DNA fragment, the OMP decarboxylase coding sequence was replaced with a kanomycin-resistance gene (aph) to create pY6015 (FIG. 3). This left intact approximately 1.5 kb of UraA flanking sequences that could be used to direct homologous integration. The transformation experiment described above for plasmid pYUB12 was repeated with pY6015 insert DNA, and the results are summarized in the Table under Experiment 2. Again, transformation efficiencies were improved substantially by exposing cultures to 1.5% glycine for 24 hours prior to harvest, and by performing the electroporation in water rather than in buffer. However, because the transformation efficiencies obtained with the linear DNA were low, we made one additional attempt to improve these efficiencies.

Cultures of *M. bovis* BCG and other slow growing mycobacteria contain large numbers of cells that are inviable or that have an exceedingly long lag time after plating. Some investigators have suggested that mycobacterial cells have an unusual ability to enter and maintain a dormant state, even when nutrients are available (Young and Cole, "Leprosy, Tuberculosis, and the New Genetics", *J. Bacteriol.*, 175:1–6 1993). We reasoned that maintenance of BCG cultures in mid-log growth might maximize the fraction of cells that were undergoing DNA synthesis and were competent to take up DNA and to incorporate it into homologous sites in the genome. A third experiment was performed, in which BCG cultures were diluted approximately 1:4 every two days over a two-month period to ensure persistent log-phase growth before transformation. The results in the Table indicate that this approach produces a significant increase in the number of transformants obtained with either the autonomously replicating vector or the linear DNA fragment.

Ten of the BCG colonies obtained in the third experiment were selected for further study after growing to adequate size for picking (24 days after plating). The ten transformants were colony purified, and DNA was prepared from each. DNA preparations from the wild type strain and the ten transformants were digested with a variety of restriction endonucleases and Southern analysis revealed that the kanomycin-resistant BCG transformants all contained vector DNA integrated into the genome. In two of the ten transformants, the transforming DNA had integrated at the homologous locus. FIG. 5 shows representative results from Southern analysis of the wild type strain and one of the BCG recombinants in which the cloned DNA integrated at the homologous locus.

Equivalents

Those skilled in the art will recognize, or be able to ascertain using not more than routine experimentation, many equivalents to the specific embodiments of the invention described herein. Such equivalents are intended to be encompassed by the following claims.

We claim:

1. A method of transforming a slow-growing mycobacterium with heterologous DNA, comprising the steps of:
   a) combining a slow-growing mycobacterium and heterologous DNA to be transformed into the slow-growing mycobacterium, thereby producing a combination; and
   b) subjecting the combination produced in step (a) to electroporation in water, under conditions sufficient for introduction of the heterologous DNA into genomic DNA of the slow-growing mycobacterium,
wherein a slow-growing mycobacterium transformed with the heterologous DNA is produced.

2. The method of claim 1 wherein the slow-growing mycobacterium of (a) have been exposed to glycine, prior to being combined with the heterologous DNA.

3. The method of claim 2 wherein the slow-growing mycobacterium is exposed to approximately 1.5% glycine present in culture medium in which the slow-growing mycobacterium is growing.

4. The method of claim 1 in which the slow-growing mycobacterium is continuously propagated in mid-log phase, prior to being combined with the heterologous DNA.

5. The method of claim 1 wherein the slow-growing mycobacterium is selected from the group consisting of: *Mycobacterium bovis* BCG, *Mycobacterium tuberculosis*, *Mycobacterium leprae*, *Mycobacterium avium*, *Mycobacterium africanum*, and *Mycobacterium intracellulare*.

6. The method of claim 5 wherein the heterologous DNA comprises DNA homologous to genomic DNA of the slow-growing mycobacterium combined in step (a) with the heterologous DNA.

7. The method of claim 6 wherein the heterologous DNA additionally comprises DNA which is not homologous to genomic DNA of the slow-growing mycobacterium combined in step (a) with the heterologous DNA.

8. A method of transforming a slow-growing mycobacterium with heterologous DNA to produce a recombinant slow-growing mycobacterium having heterologous DNA integrated into genomic DNA, comprising the steps of:

a) combining a slow-growing mycobacterium and heterologous DNA to be transformed into the slow-growing mycobacterium, thereby producing a combination; and b) subjecting the combination produced in step (a) to electroporation in water, under conditions sufficient for introduction of the heterologous DNA into genomic DNA of the slow-growing mycobacterium, wherein a recombinant slow-growing mycobacterium having heterologous DNA integrated into genomic DNA is produced.

9. The method of claim 8 wherein the slow-growing mycobacterium of step (a) has been exposed to glycine, prior to being combined with the heterologous DNA.

10. The method of claim 9 wherein the slow-growing mycobacterium is exposed to approximately 1.5% glycine present in culture medium in which the slow-growing mycobacterium is growing.

11. The method of claim 9 wherein the slow-growing mycobacterium is continuously propagated in mid-log phase, prior to being combined with the heterologous DNA.

12. The method of claim 9 wherein the slow-growing mycobacterium is selected from the group consisting of: *Mycobacterium bovis* BCG, *Mycobacterium tuberculosis*, *Mycobacterium leprae*, *Mycobacterium avium*, *Mycobacterium africanum*, and *Mycobacterium intracellulare*.

13. The method of claim 12 wherein the heterologous DNA comprises DNA homologous to genomic DNA of the slow-growing mycobacterium combined in step (a) with the heterologous DNA.

14. The method of claim 13 wherein the heterologous DNA additionally comprises DNA which is not homologous to genomic DNA of the slow-growing mycobacterium combined in step (a) with the heterologous DNA.

15. The method of claim 14 wherein the slow-growing mycobacterium is *Mycobacterium bovis* BCG and the DNA homologous to genomic DNA of the slow-growing mycobacterium is DNA contained in the *Mycobacterium bovis* BCG orotidine-5monophosphate decarboxylase gene locus or flanking sequences thereof.

16. A method of transforming a slow-growing mycobacterium to produce a recombinant slow-growing mycobacterium in which expression of an endogenous gene of interest is altered, comprising the steps of:

(a) combining the slow-growing mycobacterium and a DNA construct comprising:
 (i) DNA homologous to genomic DNA of the slow-growing mycobacterium; and
 (ii) DNA which, when integrated into genomic DNA of the slow-growing mycobacterium, alters expression of the endogenous gene of interest, thereby producing a combination; and (b) subjecting the combination produced in step (a) to electroporation under conditions sufficient for introduction of the DNA construct into the slow-growing mycobacterium and integration of the DNA construct into genomic DNA of the slow-growing mycobacterium by homologous recombination between the DNA homologous to genomic DNA in the DNA construct and genomic DNA, thereby producing a recombinant slow-growing mycobacterium in which expression of the endogenous gene of interest is altered.

17. The method of claim 16, wherein the DNA which, when integrated into genomic DNA of the slow-growing mycobacterium, alters expression of the endogenous gene of interest, is DNA nonhomologous to genomic DNA of the slow-growing mycobacterium.

18. A method of transforming a slow-growing mycobacterium to produce a recombinant slow-growing mycobacterium in which an endogenous mycobacterial gene of interest is inactivated, comprising the steps of:

(a) combining the slow-growing mycobacterium and a DNA construct comprising:
 (i) DNA homologous to genomic DNA of the slow-growing mycobacterium; and
 (ii) DNA which, when integrated into genomic DNA of the slow-growing mycobacterium, inactivates the endogenous gene of interest, thereby producing a combination, and (b) subjecting the combination produced in step (a) to electroporation under conditions sufficient for introduction of the DNA construct into the slow-growing mycobacterium and integration of the DNA construct into genomic DNA of the slow-growing mycobacterium by homologous recombination between the DNA homologous to genomic DNA in the DNA construct and genomic DNA, thereby producing a recombinant slow-growing mycobacterium in which an endogenous mycobacterial gene of interest is inactivated.

19. The method of claim 18, wherein the DNA which, when integrated into genomic DNA of the slow-growing mycobacterium, inactivates the endogenous gene of interest, is DNA nonhomologous to genomic DNA of the slow-growing mycobacterium.

20. The method of claim 18 wherein the DNA which, when integrated into genomic DNA of the slow-growing mycobacterium, inactivates the endogenous gene of interest, replaces genomic DNA necessary for expression of the endogenous mycobacterial gene of interest.

21. A method of transforming a slow-growing mycobacterium to produce a recombinant slow-growing mycobacterium in which an endogenous mycobacterial gene of interest is activated, comprising the steps of:

(a) combining the slow-growing mycobacterium and a DNA construct comprising:
 (i) DNA homologous to genomic DNA of the slow-growing mycobacterium; and
 (ii) DNA which, when integrated into genomic DNA of the slow-growing mycobacterium, activates the endogenous gene of interest, thereby producing a combination; and (b) subjecting the combination produced in step (a) to electroporation under conditions sufficient for introduction of the DNA construct into the slow-growing mycobacterium and integration of the DNA construct into genomic DNA of the slow-growing mycobacterium by homologous recombination between the DNA homologous to genomic DNA in the DNA construct and genomic DNA, thereby producing a recombinant slow-growing mycobacterium in which an endogenous mycobacterial gene of interest is activated.

22. The method of claim 21, wherein the DNA which, when integrated into genomic DNA of the slow-growing mycobacterium, activates the endogenous gene of interest, is DNA nonhomologous to genomic DNA of the slow-growing mycobacterium.

23. The method of claim 21, wherein the DNA which, when integrated into genomic DNA of the slow-growing mycobacterium, activates the endogenous gene of interest, encodes a heterologous promoter which controls expression of the endogenous mycobacterial gene of interest.

24. A method of transforming a slow-growing mycobacterium to produce a recombinant slow-growing mycobacterium in which genomic DNA of a slow-growing mycobacterium is replaced by heterologous DNA, comprising the steps of:

(a) combining the slow-growing mycobacterium and a DNA construct comprising:

(i) DNA homologous to genomic DNA of the slow-growing mycobacterium; and (ii) DNA which, when integrated into genomic DNA of the slow-growing mycobacterium, replaces genomic DNA of interest of the slow-growing mycobacterium, thereby producing a combination; and (b) subjecting the combination produced in step (a) to electroporation under conditions sufficient for introduction of the DNA construct into the slow-growing mycobacterium and integration of the DNA construct into genomic DNA of the slow-growing mycobacterium by homologous recombination between the DNA homologous to genomic DNA in the DNA construct and genomic DNA, thereby producing a recombinant slow-growing mycobacterium in which genomic DNA of the slow-growing mycobacterium is replaced by heterologous DNA.

25. The method of claim 24, wherein the DNA homologous to genomic DNA of the slow-growing mycobacterium is a genetic marker.

26. The method of claim 24, wherein the slow-growing mycobacterium is *Mycobacterium bovis* BCG and DNA homologous to genomic DNA of the slow-growing mycobacterium is DNA contained in the orotidine-5-monophosphate decarboxylase gene locus.

27. The method of claim 24, wherein the DNA construct additionally comprises DNA encoding a protein or polypeptide selected from the group consisting of: antigens, enzymes, lymphokines and immunopotentiators.

28. The method of claim 27, wherein the DNA encoding a protein or polypeptide encodes an antigen of a pathogen.

29. The method of claim 24, wherein after integration into genomic DNA of the slow-growing mycobacterium, the DNA in the DNA construct which replaces genomic DNA of interest of the slow-growing mycobacterium, is not expressed by the recombinant slow-growing mycobacterium and inactivates or activates an endogenous mycobacterial gene of interest.

* * * * *

UNITED STATES PATENT AND TRADEMARK OFFICE
CERTIFICATE OF CORRECTION

PATENT NO. : 6,022,745
DATED : February 8, 2000
INVENTOR(S) : Anna Aldovini and Richard A. Young It is certified that error appears in the above-identified patent and that said Letters Patent is hereby corrected as shown below:

At column 1, line 25, after the "Related Applications" paragraph and prior to the "Background of the Invention", insert the following paragraph:

--GOVERNMENT SUPPORT
    The invention was supported, in whole or in part, by Grant No. NIH AI26463 from The National Institutes of Health. The United States government has certain rights in the invention.--.

Signed and Sealed this

Fifteenth Day of May, 2001

Attest:

NICHOLAS P. GODICI

*Attesting Officer*   *Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
(A) LENGTH: 4394 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:1:

```
GAGCTCGACC CCGCCGCCGA AACAGAGGTG GCCCCGCAGA CCGAAAGGCC CAAGGTGCTG     60
ATCCTCGGTT CGGGGCCCAA TCGGATCGGC CAGGGTATCG AGTTCGACTA CAGCTGCGTA    120
CACGCGGCAA CCACGTTGAG CCAGGCTGGC TTTGAGACCG TGATGGTCAA CTGCAACCCG    180
GAGACCATGG TGTCCACCGA CTTCGACACC GCGGACAGGT TGTACTTCGA GCCGTTGACG    240
TTCGAGGACG TCTTGGAGGT CTACCACGCC GAAATGGAAT CCGGTAGCGG TGGCCCGGGA    300
GTGGCCGGCG TCATCGTGCA GCTCGGCGGC CAGACCCCGC TCGGCTGGCG CACCGGCTCG    360
CCGACGCCGG GTCCCGCTCG TGGGCACCCA CCGGAGGCCA TCGACCTGGC CGAGGATGCG    420
GCCGTTCGGC GACCTGCTGA GCGAGGACTG CCGGCGCCAA AGTACGGCAC CGCAACCACT    480
TTCGCCCAGG CCCGCCGGAT CGCCGAGGAG ATCGGCTATC CGGTGCTGGT GCGGCCGTCG    540
TATGTGCTCG GTGGTCGCGG CATGGAGATC GTGTATGACG AAGAAACGTT GCAGGGCTAC    600
ATCACCCGCG CCACTCAGCT ATCCCCCGAA CACCCGGTGC TCGTGCACCG CTTCCTCGAG    660
GACGCGGTCG AGATCGACGT CGACGCTCTG TGTGATGGCG CCGAGGTCTA TATCGGCGGA    720
ATCATGGAGC ACATCGAGGA GGCCGGCATC CACTCCGGTG ACTCGGCCTG TGCGCTGCCA    780
CCGGTCACGT TGGGCCGCAG CGACATCGAG AAGGTGCGTA AGGCCACTGA AGCCATTGCG    840
CATGGCATCG GCGTGGTGGG GCTGCTCAAC GTGCAGTCCG CGCTCAAGGA TGACGTGCTC    900
TACGTCCTGG AAGCCAACCC GAGAGCGAGC CGTACCGTTC CGTTTGTATC CAAGGCCACA    960
GCGGTGCCAC TCGCCAAGGC ATGCGCCCGG ATCATGTTGG GCGCCACCAT TGCCCAGCTG   1020
```

-continued

```
CGCGCCGAAG GCTTGCTGGC GGTCACCGGG GATGGCGCCC ACGCGGCGCG AAACGCCCCC      1080

ATCGCGGTCA ACCAGGCCGT GTTGCCGTTT CACCGGTTCC GGCGCGCCGA CGGGGCCGCC      1140

ATCGACTCGC TACTCGGCCC GGAGATGAAA TCGACCGGCG AGGTGATGGG CATCGACCGC      1200

GACTTCGGCA GCCGGTTCGC CAAGAGCCAG ACCGCCGCCT ACGGGTCGCT GCCGGCCCAG      1260

GGCACAGTGT TCGTGTCGGT GGCCAACCGG GACAAGCGGT CGCTGGTGTT TCCGGTCAAA      1320

CCGATTGGCC CACCTGGGTT TTCGCGTCCT TGCCACCGAA GCACCGCAGA GATCTTGCGC      1380

CGCAACGGTA TTCCCTGCGA CGACGTCCGC AAACATTTCG AGCCGGCGCA GCCCGGCCGC      1440

CCCACAATGT CGGCGGTGGA CGCGATCCGA GCCGGCGAGG TCAACATGGT GATCAACACT      1500

CCCTATGGCA ACTCCGGTCC GCGCATCGAC GGCTATGAGA TCCGTTCGGC GGCGGTGGCC      1560

GGCAACATCC CGTGCATCAC CACGGTGCAG GGCGCATCCG CCGCCGTGCA GGGGATAGAG      1620

GCCGGGATCC GCGGCGACAT CGGGGTGCGC TCCCTGCAGG AGCTGCACCG GGTGATCGGG      1680

GGCGTCGAGC GGTGACCGGG TTCGGTCTCC GGTTGGCCGA GGCAAAGGCA CGCCGCGGCC      1740

CGTTGTGTCT GGGCATCGAT CCGCATCCCG AGCTGCTGCG GGGCTGGGAT CTGGCGACCA      1800

CGGCCGACGG GCTGGCCGCG TTCTGCGACA TCTGCGTACG GGCCTTCGCT GATTTCGCGG      1860

TGGTCAAACC GCAGGTGGCG TTTTTTGAGT CATACGGGGC TGCCGGATTC GCGGTGCTGG      1920

AGCGCACCAT CGCGGAACTG CGGGCCGCAG ACGTGCTGGT GTTGGCCGAC GCCAAGCGCG      1980

GCGACATTGG GGCGACCATG TCGGCGTATG CGACGGCCTG GGTGGGCGAC TCGCCGCTGG      2040

CCGCCGACGC CGTGACGGCC TCGCCCTATT TGGGCTTCGG TTCGCTGCGG CCGCTGCTAG      2100

AGGTCGCGGC CGCCCACGGC CGAGGGGTGT TCGTGCTGGC GGCCACCTCC AATCCCGAGG      2160

GTGCGGCGGT GCAGAATGCC GCCGCCGACG GCCGCAGCGT GGCCCAGTTG GTCGTGGACC      2220

AGGTGGGGGC GGCCAACGAG GCGGCAGGAC CCGGGCCCGG ATCCATCGGC GTGGTCGTCG      2280

GCGCAACGGC GCCACAGGCC CCCGATCTCA GCGCCTTCAC CGGGCCGGTG CTGGTGCCCG      2340

GCGTGGGGGT GCAGGGCGGG CGCCCGGAGG CGCTGGGCGG TCTGGGCGGG GCCGCATCGA      2400

GCCAGCTGTT GCCCGCGGTG GCGCGCGAGG TCTTGCGGGC CGGCCCCGGC GTGCCCGAAT      2460

TGCGCGCCGC GGGCGAACGG ATGCGCGATG CCGTCGCCTA TCTCGCTGCC GTGTAGCGGG      2520

TGCCCTGCCA CCGCGCCGCT AAATCCCACC AGCATGGGGT GGTGAGCCCA GCGCTCGTGT      2580

GACCAAACTC ACCGCCCTGG GCCGTCGTCA CGCTGTGTTA ACCTCTCGTT CAAATGATAT      2640

TCATATTCAA TAGTGGCGCT AAGTGTCCGG TTGAATCCCC GTTGAACCCC CAACAGATGG      2700

AGTCTGTGTC GTGACGTTGC GAGTCGTTCC CGAAAGCCTG GCAGGCGCCA GCGCTGCCAT      2760

CGAAGCAGTG ACCGCTCGCC TGGCCGCCGC GCACGCCGCG GCGGCCCCGT TTATCGCGGC      2820

GGTCATCCCG CCTGGGTCCG ACTCGGTTTC GGTGTGCAAC GCCGTTGAGT TCAGCGTTCA      2880

CGGTAGTCAG CATGTGGCAA TGGCCGCTCA GGGGGTTGAG GAGCTCGGCC GCTCGGGGGT      2940

CGGGGTGGCC GAATCGGGTG CCAGTTATGC CGCTAGGATG CGCTGGCGGC GGCGTCGTAT      3000

CTCAGCGGTG GGCTATGACC GAGCCGTGGA TAGCCTTCCC TCCCGAGGTG CACTCGGCGA      3060

TGCTGAACTA CGGTGCGGGC GTTGGGCCGA TGTTGATCTC CGCCACGCAG AATGGGAGC      3120

TCAGCGCCCA ATACGCAGAA GCGGCATCCG AGGTCGAGGA ATTGTTGGGG GTGGTGGCCT      3180

CCGAGGGATG GCAGGGGCAA GCCGCCGAGG CGTTAGTCGC CGCGTACATG CCGTTTCTGG      3240

CGTGGCTGAT CCAAGCCAGC GCCGACTGCG TGGAAATGGC CGCCCAGCAA CACGCCGTCA      3300

TCGAGGCCTA CACTGCCGCG GTAGAGCTGA TGCCTACTCA GGTCGAACTG GCCGCCAACC      3360

AAATCAAGCT CGCGGTGTTG GTAGCGACCA ATTTCTTTGG CATCAACACC ATTCCCATTG      3420
```

```
CGATCAATGA GGCCGAGTAC GTGGAGATGT GGGTTCGGGC CGCCACCACG ATGGCGACCT      3480

ATTCAACAGT CTCCAGATCG GCGCTCTCCG CGATGCCGCA CACCAGCCCC CCGCCGCTGA      3540

TCCTGAAATC CGATGAACTG CTCCCCGACA CCGGGGAGGA CTCCGATGAA GACGGCCACA      3600

ACCATGGCGG TCACAGTCAT GGCGGTCACG CCAGGATGAT CGATAACTTC TTTGCCGAAA      3660

TCCTGCGTGG CGTCAGCGCG GGCCGCATTG TTTGGGACCC CGTCAACGGC ACCCTCAACG      3720

GACTCGACTA CGACGATTAC GTCTACCCCG GTCACGCGAT CTGGTGGCTG GCTCGAGGCC      3780

TCGAGTTTTT TCAGGATGGT GAACAATTTG GCGAACTGTT GTTCACCAAT CCGACTGGGG      3840

CTTTTCAGTT CCTCCTCTAC GTCGTTGTGG TGGATTTGCC GACGCACATA GCCCAGATCG      3900

CTACCTGGCT GGGCCAGTAC CCGCAGTTGC TGTCGGCTGC CCTCACTGGC GTCATCGCCC      3960

ACCTGGGAGC AATAACTGGT TTGGCGGGCC TATCCGGCCT GAGCGCCATT CCGTCTGCTG      4020

CGATACCCGC CGTTGTACCG GAGCTGACAC CCGTCGCGGC CGCGCCGCCT ATGTTGGCGG      4080

TCGCCGGGGT GGGCCCTGCA GTCGCCGCGC CGGGCATGCT CCCCGCCTCA GCACCCGCAC      4140

CGGCGGCAGC GGCCGGCGCC ACCGCAGCCG GCCCGACGCC GCCGGCGACT GGTTTCGGAG      4200

GGCTTCCCGC CCTACCTGGT CGGCGGTGGC GGCCCAGGAA TAGGGTTCGG CTCGGGACAG      4260

TCGGCCCACG CCAAGGCCGC GGCGTCCGAT TCCGCTGCAG CCGAGTCGGC GGCCCAGGCC      4320

TCGGCGCGTG CGCAGGCGCG TGCTGCACGG CGGGGCCGCT CGGCGGCAAG GCACGTGGCC      4380

ATCGTGACGA ATTC                                                       4394

(2) INFORMATION FOR SEQ ID NO:2:

(i) SEQUENCE CHARACTERISTICS:
        (A) LENGTH: 1271 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Glu Leu Asp Pro Ala Ala Glu Thr Glu Val Ala Pro Gln Thr Glu Arg
1               5                   10                  15

Pro Lys Val Leu Ile Leu Gly Ser Gly Pro Asn Arg Ile Gly Gln Gly
            20                  25                  30

Ile Glu Phe Asp Tyr Ser Cys Val His Ala Ala Thr Thr Leu Ser Gln
        35                  40                  45

Ala Gly Phe Glu Thr Val Met Val Asn Cys Asn Pro Glu Thr Met Val
    50                  55                  60

Ser Thr Asp Phe Asp Thr Ala Asp Arg Leu Tyr Phe Glu Pro Leu Thr
65                  70                  75                  80

Phe Glu Asp Val Leu Glu Val Tyr His Ala Glu Met Glu Ser Gly Ser
                85                  90                  95

Gly Gly Pro Gly Val Ala Gly Val Ile Val Gln Leu Gly Gly Gln Thr
            100                 105                 110

Pro Leu Gly Trp Arg Thr Gly Ser Pro Thr Pro Gly Pro Ala Arg Gly
        115                 120                 125

His Pro Pro Glu Ala Ile Asp Leu Ala Glu Asp Ala Ala Val Arg Arg
    130                 135                 140

Pro Ala Glu Arg Gly Leu Pro Ala Pro Lys Tyr Gly Thr Ala Thr Thr
145                 150                 155                 160

Phe Ala Gln Ala Arg Arg Ile Ala Glu Glu Ile Gly Tyr Pro Val Leu
```

-continued

```
                165                 170                 175
Val Arg Pro Ser Tyr Val Leu Gly Gly Arg Gly Met Glu Ile Val Tyr
                    180                 185                 190

Asp Glu Glu Thr Leu Gln Gly Tyr Ile Thr Arg Ala Thr Gln Leu Ser
                195                 200                 205

Pro Glu His Pro Val Leu Val His Arg Phe Leu Glu Asp Ala Val Glu
            210                 215                 220

Ile Asp Val Asp Ala Leu Cys Asp Gly Ala Glu Val Tyr Ile Gly Gly
225                 230                 235                 240

Ile Met Glu His Ile Glu Glu Ala Gly Ile His Ser Gly Asp Ser Ala
                    245                 250                 255

Cys Ala Leu Pro Pro Val Thr Leu Gly Arg Ser Asp Ile Glu Lys Val
                260                 265                 270

Arg Lys Ala Thr Glu Ala Ile Ala His Gly Ile Gly Val Val Gly Leu
            275                 280                 285

Leu Asn Val Gln Ser Ala Leu Lys Asp Asp Val Leu Tyr Val Leu Glu
        290                 295                 300

Ala Asn Pro Arg Ala Ser Arg Thr Val Pro Phe Val Ser Lys Ala Thr
305                 310                 315                 320

Ala Val Pro Leu Ala Lys Ala Cys Ala Arg Ile Met Leu Gly Ala Thr
                    325                 330                 335

Ile Ala Gln Leu Arg Ala Glu Gly Leu Leu Ala Val Thr Gly Asp Gly
                340                 345                 350

Ala His Ala Ala Arg Asn Ala Pro Ile Ala Val Asn Gln Ala Val Leu
            355                 360                 365

Pro Phe His Arg Phe Arg Arg Ala Asp Gly Ala Ala Ile Asp Ser Leu
        370                 375                 380

Leu Gly Pro Glu Met Lys Ser Thr Gly Glu Val Met Gly Ile Asp Arg
385                 390                 395                 400

Asp Phe Gly Ser Arg Phe Ala Lys Ser Gln Thr Ala Ala Tyr Gly Ser
                    405                 410                 415

Leu Pro Ala Gln Gly Thr Val Phe Val Ser Val Ala Asn Arg Asp Lys
                420                 425                 430

Arg Ser Leu Val Phe Pro Val Lys Arg Leu Ala His Leu Gly Phe Arg
            435                 440                 445

Val Leu Ala Thr Glu Ala Pro Gln Arg Ser Cys Ala Ala Thr Val Phe
        450                 455                 460

Pro Ala Thr Thr Ser Ala Asn Ile Ser Ser Arg Arg Ser Pro Ala Ala
465                 470                 475                 480

Pro Gln Cys Arg Arg Trp Thr Arg Ser Glu Pro Ala Arg Ser Thr Trp
                    485                 490                 495

Met Thr Gly Phe Gly Leu Arg Leu Ala Glu Ala Lys Ala Arg Arg Gly
                500                 505                 510

Pro Leu Cys Leu Gly Ile Asp Pro His Pro Glu Leu Leu Arg Gly Trp
            515                 520                 525

Asp Leu Ala Thr Thr Ala Asp Gly Leu Ala Ala Phe Cys Asp Ile Cys
        530                 535                 540

Val Arg Ala Phe Ala Asp Phe Ala Val Val Lys Pro Gln Val Ala Phe
545                 550                 555                 560

Phe Glu Ser Tyr Gly Ala Ala Gly Phe Ala Val Leu Glu Arg Thr Ile
                    565                 570                 575

Ala Glu Leu Arg Ala Ala Asp Val Leu Val Leu Ala Asp Ala Lys Arg
                580                 585                 590
```

-continued

```
Gly Asp Ile Gly Ala Thr Met Ser Ala Tyr Ala Thr Ala Trp Val Gly
            595                 600                 605

Asp Ser Pro Leu Ala Ala Asp Ala Val Thr Ala Ser Pro Tyr Leu Gly
        610                 615                 620

Phe Gly Ser Leu Arg Pro Leu Glu Val Ala Ala Ala His Gly Arg
625                 630                 635                 640

Gly Val Phe Val Leu Ala Ala Thr Ser Asn Pro Glu Gly Ala Ala Val
                645                 650                 655

Gln Asn Ala Ala Ala Asp Gly Arg Ser Val Ala Gln Leu Val Val Asp
            660                 665                 670

Gln Val Gly Ala Ala Asn Glu Ala Ala Gly Pro Gly Pro Gly Ser Ile
        675                 680                 685

Gly Val Val Gly Ala Thr Ala Pro Gln Ala Pro Asp Leu Ser Ala
690                 695                 700

Phe Thr Gly Pro Val Leu Val Pro Gly Val Gly Val Gln Gly Gly Arg
705                 710                 715                 720

Pro Glu Ala Leu Gly Gly Leu Gly Gly Ala Ser Ser Gln Leu Leu
                725                 730                 735

Pro Ala Val Ala Arg Glu Val Leu Arg Ala Gly Pro Gly Val Pro Glu
            740                 745                 750

Leu Arg Ala Ala Gly Glu Arg Met Arg Asp Ala Val Ala Tyr Leu Ala
        755                 760                 765

Ala Val Met Trp Gln Trp Pro Leu Arg Gly Leu Arg Ser Ser Ala Ala
        770                 775                 780

Arg Gly Ser Gly Trp Pro Asn Arg Val Pro Val Met Pro Leu Gly Cys
785                 790                 795                 800

Ala Gly Gly Gly Val Val Ser Gln Arg Trp Ala Met Thr Glu Pro Trp
                805                 810                 815

Ile Ala Phe Pro Pro Glu Val His Ser Ala Met Leu Asn Tyr Gly Ala
            820                 825                 830

Gly Val Gly Pro Met Leu Ile Ser Ala Thr Gln Asn Gly Glu Leu Ser
        835                 840                 845

Ala Gln Tyr Ala Glu Ala Ala Ser Glu Val Glu Glu Leu Leu Gly Val
    850                 855                 860

Val Ala Ser Glu Gly Trp Gln Gly Gln Ala Ala Glu Ala Leu Val Ala
865                 870                 875                 880

Ala Tyr Met Pro Phe Leu Ala Trp Leu Ile Gln Ala Ser Ala Asp Cys
                885                 890                 895

Val Glu Met Ala Ala Gln Gln His Ala Val Ile Glu Ala Tyr Thr Ala
            900                 905                 910

Ala Val Glu Leu Met Pro Thr Gln Val Glu Leu Ala Ala Asn Gln Ile
        915                 920                 925

Lys Leu Ala Val Leu Val Ala Thr Asn Phe Phe Gly Ile Asn Thr Ile
    930                 935                 940

Pro Ile Ala Ile Asn Glu Ala Glu Tyr Val Glu Met Trp Val Arg Ala
945                 950                 955                 960

Ala Thr Thr Met Ala Thr Tyr Ser Thr Val Ser Arg Ser Ala Leu Ser
                965                 970                 975

Ala Met Pro His Thr Ser Pro Pro Leu Ile Leu Lys Ser Asp Glu
            980                 985                 990

Leu Leu Pro Asp Thr Gly Glu Asp Ser Asp Glu Asp Gly His Asn His
        995                 1000                1005
```

```
Gly Gly His Ser His Gly Gly His Ala Arg Met Ile Asp Asn Phe Phe
        1010            1015            1020

Ala Glu Ile Leu Arg Gly Val Ser Ala Gly Arg Ile Val Trp Asp Pro
1025            1030            1035            1040

Val Asn Gly Thr Leu Asn Gly Leu Asp Tyr Asp Tyr Val Tyr Pro
                1045            1050            1055

Gly His Ala Ile Trp Trp Leu Ala Arg Gly Leu Glu Phe Phe Gln Asp
            1060            1065            1070

Gly Glu Gln Phe Gly Glu Leu Leu Phe Thr Asn Pro Thr Gly Ala Phe
        1075            1080            1085

Gln Phe Leu Leu Tyr Val Val Val Asp Leu Pro Thr His Ile Ala
    1090            1095            1100

Gln Ile Ala Thr Trp Leu Gly Gln Tyr Pro Gln Leu Leu Ser Ala Ala
1105            1110            1115            1120

Leu Thr Gly Val Ile Ala His Leu Gly Ala Ile Thr Gly Leu Ala Gly
                1125            1130            1135

Leu Ser Gly Leu Ser Ala Ile Pro Ser Ala Ala Ile Pro Ala Val Val
            1140            1145            1150

Pro Glu Leu Thr Pro Val Ala Ala Pro Pro Met Leu Ala Val Ala
        1155            1160            1165

Gly Val Gly Pro Ala Val Ala Ala Pro Gly Met Leu Pro Ala Ser Ala
    1170            1175            1180

Pro Ala Pro Ala Ala Ala Ala Gly Ala Thr Ala Ala Gly Pro Thr Pro
1185            1190            1195            1200

Pro Ala Thr Gly Phe Gly Gly Leu Pro Ala Leu Pro Gly Arg Arg Trp
                1205            1210            1215

Arg Pro Arg Asn Arg Val Arg Leu Gly Thr Val Gly Pro Arg Gln Gly
            1220            1225            1230

Arg Gly Val Arg Phe Arg Cys Ser Arg Val Gly Gly Pro Gly Leu Gly
            1235            1240            1245

Ala Cys Ala Gly Ala Cys Cys Thr Ala Gly Pro Leu Gly Gly Lys Ala
        1250            1255            1260

Arg Gly His Arg Asp Glu Phe
1265            1270
```